(12) United States Patent
Everhart et al.

(10) Patent No.: US 11,833,404 B2
(45) Date of Patent: Dec. 5, 2023

(54) PERSONALIZED ADJUSTED YARDAGE RECOMMENDATION SYSTEMS

(71) Applicant: PRECISION PRO SPORTS, LLC, Cincinnati, OH (US)

(72) Inventors: Alex Everhart, Cincinnati, OH (US); Nick Ellis, Beavercreek, OH (US); Brayden Epp, Cincinnati, OH (US)

(73) Assignee: PRECISION PRO SPORTS, LLC, Cincinnati, OH (US)

( * ) Notice: Subject to any disclaimer, the term of this patent is extended or adjusted under 35 U.S.C. 154(b) by 0 days.

(21) Appl. No.: 17/341,514

(22) Filed: Jun. 8, 2021

(65) Prior Publication Data

US 2022/0111282 A1 Apr. 14, 2022

Related U.S. Application Data

(60) Provisional application No. 63/188,584, filed on May 14, 2021, provisional application No. 63/089,173, filed on Oct. 8, 2020.

(51) Int. Cl.
*A63B 69/36* (2006.01)
*A63B 24/00* (2006.01)
(Continued)

(52) U.S. Cl.
CPC ...... *A63B 69/3605* (2020.08); *A63B 24/0021* (2013.01); *A63B 71/0622* (2013.01);
(Continued)

(58) Field of Classification Search
CPC ............ A63B 69/3605; A63B 71/0622; A63B 24/0021; A63B 2071/0691;
(Continued)

(56) References Cited

U.S. PATENT DOCUMENTS

| | | | | |
|---|---|---|---|---|
| 4,136,394 A | * | 1/1979 | Jones | G01S 11/16 367/128 |
| 4,531,052 A | * | 7/1985 | Moore | G01C 3/22 235/407 |

(Continued)

FOREIGN PATENT DOCUMENTS

| | | |
|---|---|---|
| EP | 1647835 B1 | 11/2012 |
| TW | M562386 U | 6/2018 |

OTHER PUBLICATIONS

Burglund et al., "Golf Ball Flight Dynamics", May 13, 2011, pp. 1-19 (19 pages).

(Continued)

*Primary Examiner* — Jeffrey S Vanderveen
(74) *Attorney, Agent, or Firm* — Daniel H. Lajiness; Daniel F. Nesbitt; Nesbitt IP LLC

(57) ABSTRACT

Systems, methods, and devices for providing an adjusted yardage recommendation (AYR) to a golfer prior to a golf shot. AYRs are determined based on predicted golf ball trajectories that are modeled from a golfer's golf ball launch data, using non-classical mathematical approximation methods. Each of the modeled trajectories are unique, and result in personalized AYR values that are personalized to each individual golfer, even where two golfers hit a ball with the same club the same distance while having two different ball flights. Devices that can perform the methods of the present invention include rangefinder devices and/or portable computing devices, such as a smartphone. Systems can include a rangefinder device and a portable computing device, in which the rangefinder device determines the line-of-sight distance and angle of elevation to a target and communicates the same to the portable computing device, which calculates the AYR.

20 Claims, 13 Drawing Sheets

(51) Int. Cl.
    *A63B 71/06*     (2006.01)
    *G01C 3/06*      (2006.01)
    *H04W 12/50*     (2021.01)
    *H04W 4/80*      (2018.01)

(52) U.S. Cl.
    CPC .............. *G01C 3/06* (2013.01); *H04W 4/80* (2018.02); *H04W 12/50* (2021.01); *A63B 2024/0056* (2013.01); *A63B 2071/0691* (2013.01); *A63B 2220/16* (2013.01); *A63B 2220/20* (2013.01); *A63B 2225/50* (2013.01)

(58) Field of Classification Search
    CPC ........ A63B 2220/20; A63B 2024/0056; A63B 2225/50; A63B 2220/16; H04W 4/80; H04W 12/50; G01C 3/06
    See application file for complete search history.

(56) References Cited

U.S. PATENT DOCUMENTS

| | | | | |
|---|---|---|---|---|
| 4,561,204 A * | 12/1985 | Binion | ...................... | F41G 3/06 |
| | | | | D16/132 |
| 4,777,352 A * | 10/1988 | Moore | ...................... | G06T 7/60 |
| | | | | 235/407 |
| 4,965,439 A * | 10/1990 | Moore | ...................... | F41G 3/06 |
| | | | | 702/158 |
| 5,283,732 A * | 2/1994 | Mauritz | ................. | G06Q 30/02 |
| | | | | 473/407 |
| 5,294,110 A * | 3/1994 | Jenkins | .............. | A63B 69/3623 |
| | | | | 473/407 |
| 5,311,271 A * | 5/1994 | Hurt | ........................ | G01S 17/36 |
| | | | | 356/5.1 |
| 5,479,712 A * | 1/1996 | Hargrove | ................ | F41G 1/473 |
| | | | | 33/262 |
| 5,686,690 A * | 11/1997 | Lougheed | ............... | F41A 17/08 |
| | | | | 89/134 |
| 5,806,020 A * | 9/1998 | Zykan | .................... | G01S 17/08 |
| | | | | 250/201.6 |
| 5,859,693 A * | 1/1999 | Dunne | .................. | G01C 15/002 |
| | | | | 356/141.2 |
| 5,914,775 A * | 6/1999 | Hargrove | ................ | G01C 3/08 |
| | | | | 356/3.13 |
| 5,926,260 A * | 7/1999 | Dunne | .................. | G04F 10/105 |
| | | | | 356/5.1 |
| 6,533,674 B1 * | 3/2003 | Gobush | .................... | G01P 3/38 |
| | | | | 473/409 |
| 6,873,406 B1 * | 3/2005 | Hines | .................... | G01S 7/4808 |
| | | | | 356/5.01 |
| 7,118,498 B2 * | 10/2006 | Meadows | .......... | A63B 71/0669 |
| | | | | 473/409 |
| 7,239,377 B2 * | 7/2007 | Vermillion | .............. | G01S 17/86 |
| | | | | 356/5.01 |
| 7,395,696 B2 * | 7/2008 | Bissonnette | ....... | A63B 69/3623 |
| | | | | 73/65.03 |
| 7,535,553 B2 | 5/2009 | Vermillion et al. | | |
| 7,654,029 B2 * | 2/2010 | Peters | ...................... | F41G 3/08 |
| | | | | 42/114 |
| 7,658,031 B2 * | 2/2010 | Cross | ........................ | F41G 3/02 |
| | | | | 42/142 |
| 7,859,650 B2 | 12/2010 | Vermillion et al. | | |
| 8,081,298 B1 * | 12/2011 | Cross | ........................ | F41G 3/02 |
| | | | | 356/3.01 |
| 8,172,702 B2 * | 5/2012 | Meadows | ............... | G01S 19/19 |
| | | | | 473/407 |
| 8,282,493 B2 | 10/2012 | Román et al. | | |
| 8,314,923 B2 * | 11/2012 | York | ...................... | A63B 71/06 |
| | | | | 356/5.1 |
| 8,500,563 B2 | 8/2013 | Román et al. | | |
| 8,512,162 B2 * | 8/2013 | Kim | .................. | G09B 19/0038 |
| | | | | 473/407 |
| 8,529,380 B1 * | 9/2013 | Hubenthal | ............. | G06Q 30/02 |
| | | | | 473/223 |
| 8,556,267 B2 * | 10/2013 | Gobush | .................. | A63B 71/06 |
| | | | | 273/317.2 |
| 9,377,302 B2 * | 6/2016 | Frischman | ............ | G01S 7/4814 |
| 10,350,453 B2 * | 7/2019 | Niegowski | ......... | A63B 24/0021 |
| 10,682,562 B2 | 6/2020 | Syed et al. | | |
| 2004/0087384 A1 * | 5/2004 | Sosin | ..................... | A63B 60/46 |
| | | | | 473/289 |
| 2005/0021282 A1 * | 1/2005 | Sammut | ................... | F41G 1/473 |
| | | | | 702/181 |
| 2005/0221905 A1 * | 10/2005 | Dunne | ................... | A63B 57/00 |
| | | | | 473/131 |
| 2007/0197314 A1 * | 8/2007 | York | ...................... | A63B 69/36 |
| | | | | 473/407 |
| 2008/0182685 A1 * | 7/2008 | Marty | .................... | A63B 69/38 |
| | | | | 473/407 |
| 2009/0088275 A1 * | 4/2009 | Solheim | ............. | A63B 69/3605 |
| | | | | 473/409 |
| 2011/0299729 A1 * | 12/2011 | Dawe | ...................... | G06T 7/246 |
| | | | | 382/103 |
| 2013/0184091 A1 * | 7/2013 | Rauchholz | ............. | A63B 60/22 |
| | | | | 473/238 |
| 2014/0191896 A1 * | 7/2014 | Johnson | .................. | G01S 13/58 |
| | | | | 342/104 |
| 2015/0343292 A1 * | 12/2015 | Leech | ................ | G02B 27/0172 |
| | | | | 700/91 |
| 2016/0320476 A1 * | 11/2016 | Johnson | ................ | G01S 13/867 |
| 2017/0001072 A1 * | 1/2017 | Brekke | .................. | G16H 20/30 |
| 2017/0274256 A1 * | 9/2017 | Brekke | .................. | A63B 60/42 |
| 2017/0304705 A1 * | 10/2017 | Hermandorfer | ... | A63B 69/0002 |
| 2018/0178069 A1 * | 6/2018 | Sato | ..................... | A63B 37/0096 |
| 2018/0200605 A1 * | 7/2018 | Syed | ..................... | A63B 69/3605 |
| 2020/0023235 A1 * | 1/2020 | Hermansen | .......... | A63B 69/002 |
| 2020/0197747 A1 * | 6/2020 | Broadie | ............. | A63B 71/0622 |
| 2020/0200530 A1 * | 6/2020 | Nyhart | .................... | G01S 17/86 |
| 2020/0217955 A1 * | 7/2020 | DeCastro | ................ | G01S 17/08 |
| 2020/0406118 A1 * | 12/2020 | Buscemi | ............... | A63B 47/021 |
| 2021/0069548 A1 * | 3/2021 | Beach | .................... | A63B 60/46 |
| 2021/0141588 A1 * | 5/2021 | DeCastro | ................ | H04R 3/00 |
| 2021/0144478 A1 | 5/2021 | Decastro et al. | | |
| 2021/0220718 A1 * | 7/2021 | Tuxen | .................. | A63B 69/3623 |
| 2021/0260443 A1 * | 8/2021 | Broadie | ............. | A63B 71/0622 |

OTHER PUBLICATIONS

Abassy, "Introduction to Piecewise Analytic Method", Jul. 2012, Proc. of the 4th. Symb. of Frac. Calcu. Appl. Faculty of Science Alexandria University, Alexandria, Egypt, p. 1-19 (19 pages).
Foresight Sports, "An Introduction to Understanding Ball Launch & Club Data", 2013 (14 pages).
Walnaina et al., "Simulation of Dimple Characteristics on the Trajectories of a Dimpled Sphere (Golf Ball) in Motion", 2018, J. Appl. Computat. Math., vol. 7 No. 1, pp. 1-9 (9 pages).
Leupold, Golf Catalog, 2018, p. 1-10 (10 pages).
Abassy, "Piecewise Analytic Method VS Runge-Kutta Method (Comparative Study)", Feb. 2019, Science Publishing Corporation, vol. 9 No. 2, pp. 1-12 (12 pages).
European Search Report dated Nov. 8, 2006, for EP Application No. 05009253.5 filed Apr. 27, 2005, now EP Patent No. 1647835 (4 pages).
"OPTI-Logic XT-Series Tilt-Compensated Laser Rangefinder Manual", Nov. 8, 2006 according to Wayback Machine, OPTI-Logic Corporation (4 pages).
Walker, "Fundamentals of Physics (Halliday & Resnick)", 10$^{th}$ ed., 2014, John Wiley & Sons Inc., Chapter 4 Section 4—"Projectile Motion", p. 70-75 (8 pages).
International Search Report and Written Opinion dated Feb. 2, 2022 in related International Application No. PCT/US2021/053900 filed Oct. 7, 2021 (16 pages).
Penner, "The physics of golf", Dec. 20, 2002, Reports on Progress in Physics, vol. 66, p. 131-171 (41 pages).

* cited by examiner

PERSONALIZED ADJUSTED YARDAGE RECOMMENDATION SYSTEMS

CROSS-REFERENCE TO RELATED APPLICATIONS

This application claims the benefit of U.S. Provisional Application No. 63/089,173, filed on Oct. 8, 2020, and U.S. Provisional Application No. 63/188,584, filed on May 14, 2021, the disclosures of which are incorporated by reference in their entireties.

FIELD OF THE INVENTION

The present invention relates to methods, devices, and systems for determining a personalized, adjusted distance to a golf target, prior to hitting a golf shot.

BACKGROUND OF THE INVENTION

One of the most important factors in the success of a golf shot is the golfer's ability to determine the distance to his or her target. Generally, golf courses provide markers that provide the distance to the center of the green, either on sprinkler heads scattered throughout the golf hole, or a series of markers that are typically arranged 100, 150, and 200 yards away. However, it is up to the golfer to determine the distance to a different target, such as a pin located on a different portion of a green, a hazard, a tree, and/or other structural feature associated with a golf hole.

To assist a golfer in determining the distance to a target, golf companies have developed laser rangefinders and global positioning system (GPS) devices. However, many of these devices are only capable of giving the absolute, or line-of-sight (LOS), distance to the target, and do not factor in the elevation of the target relative to the golfer. Therefore, with these devices, the golfer must still estimate how many yards or meters to either add or subtract to the LOS distance to determine an adjusted distance to the target.

Recently-developed devices and/or applications have sought to address this issue by providing an adjusted distance to the golfer. U.S. Pat. Nos. 7,239,377, 7,535,553, and 7,859,650, herein incorporated by reference in their entireties, describe rangefinder devices having a laser range sensor, a tilt sensor for determining an angle to a target relative to the device, and a computing element for determining an adjusted distance based on an assumed parabolic trajectory of a golf ball, and the flat ground distance that the golf ball must travel so the parabolic trajectory intersects the target. U.S. Pat. No. 8,314,923, herein incorporated by reference in its entirety, describes a laser rangefinder device that similarly calculates an adjusted distance based on the LOS distance and angle to the target, based in-part on factors such as "hitting ability," which corresponds with the user input of average shot distances when using one or more clubs.

Similarly, adjusted yardage recommendations can be made based on the actual results of golf shots made by the golfer. U.S. Pat. No. 8,529,380, herein incorporated by reference in its entirety, describes methods for providing a golf club recommendation that utilize user data and golf club data including average shot distances to determine the recommended club, and updating subsequent recommendations based on the shot result. U.S. Pat. No. 10,682,562, herein incorporated by reference in its entirety, describes an autonomous personalized golf recommendation and analysis environment that uses artificial intelligence and machine learning to analyze the distances of actual golf shots in order to provide personalized recommendations to the golfer, such as the identity of a club to use for a particular shot and an estimated distance that the golfer should hit the shot, based on a desired golf target, such as a portion of the green or user-defined location on a golf hole.

However, none of the above patents, or the devices, systems, or methods disclosed therein, utilize or describe personalized trajectories which can be used to provide a yardage recommendation. Personalized trajectories can be useful to more accurately predict a golfer's actual ball flight, as well as distinguish between a first golfer from a second golfer, where both golfers can hit a golf ball the same distance with a particular club, but the second golfer typically hits the ball higher or lower than the first golfer. Therefore, there remains a need for devices, systems, and methods that can more accurately predict the trajectory of a golf shot, so that a better adjusted yardage or club recommendation can be made that is personalized for each individual golfer.

SUMMARY OF THE INVENTION

The present invention provides methods, devices, and systems for determining a personalized, adjusted yardage recommendation (AYR) for a golfer trying to hit a golf ball to a golf target. The AYRs are determined in part from predicted golf ball trajectories that can be unique to each individual golfer, and more particularly for each club within the golfer's bag. When the golf target is either above or below the golfer, a predicted trajectory can be utilized to determine an adjusted distance that accounts for the change in elevation, which can aid in club selection. In some embodiments, the AYR can be provided along with a club recommendation.

In an aspect of the invention, a method for providing an AYR for a golf shot can comprise the following steps: (a) accumulating shot data associated with one or more golf clubs, the shot data comprising an average shot distance ($\bar{x}$) and golf ball launch data, the golf ball launch data comprising at least one, and preferably all, of an initial ball speed, initial backspin rate, and launch angle; (b) selecting the one or more of the golf clubs having the accumulated shot data; (c) predicting a personalized trajectory a for golf shot taken using each of the one or more selected golf clubs, by performing at least one discretized mathematical approximation, wherein the at least one mathematical approximation utilizes the golf ball launch data for each of the one or more selected golf clubs to determine an x-position, a y-position, a velocity, and an angle-of-flight ($\varphi$) relative to the x-axis, at a plurality of discretized points along the predicted personalized trajectory; (d) determining a horizontal distance (x) and an elevation (y) of a golf target relative to a location of the golf shot, to calculate an x-coordinate position ($x_t$) and a y-coordinate position ($y_t$) for the golf target; (e) comparing the predicted personalized trajectory for each of the one or more selected golf clubs with the calculated $x_t$ and $y_t$ for the golf target; (f) choosing a golf club from among the one or more selected golf clubs, wherein the chosen golf club has a point (x',y') along its predicted personalized trajectory in which when y' is equal to $y_t$, x' is greater or equal to $x_t$; and (g) calculating a personalized AYR by applying the formula, $$AYR = \bar{x} \cdot \left(\frac{x_t}{x'}\right),$$

for the chosen golf club. In another embodiment, the average shot distance, $\bar{x}$, associated with a particular golf club can refer to an average "carry" distance, which is the average distance the golf ball travels in the air until landing. Some non-limiting examples in which the average carry distance can be useful can include: determining an AYR to a flag or other portion of the green; or for determining an AYR for hitting the ball over a hazard, sand trap, or other course feature. In another embodiment, the average shot distance, $\bar{x}$, associated with a particular golf club can refer to an average "total" distance, which is the average distance the golf ball travels from the moment it was struck until the moment the ball stops. As a result, the total distance is the carry distance plus any additional distance resulting from bouncing and/or rolling on the ground. Some non-limiting examples in which the average total distance can be useful can include: determining an AYR for a drive or other shot off the tee; ensuring that the ball stays short of a particular hazard, sand trap, or other course feature; and/or for ensuring that the golf ball is positioned in an optimal position and/or angle for the next shot, such as hitting the ball past the corner of a dogleg, while ensuring that the ball remains in the fairway without rolling into the rough.

When y=0, such as when the terrain is flat, the AYR is the same as the horizontal distance, x. However, in various embodiments, when y≠0, the values of x and y can be derived from the line-of-sight (LOS) distance from the golf target. In some embodiments, the LOS distance can be can be determined by a rangefinder device. From the LOS distance, the horizontal distance, x, can be derived by multiplying the LOS distance by the cosine of the angle of elevation (θ) between the device and the target, and the elevation, y, can be derived by multiplying the LOS distance by the sine of the angle of elevation (θ) between the device and the target.

In another aspect, the invention provides a system for determining an AYR, useful for assisting a player in selecting a golf club prior to a golf shot, the system comprising: (a) a rangefinder device comprising (i) a range sensor for determining a line-of-sight distance between the rangefinder device and a golf target; (ii) an angle sensor for determining an angle of elevation between the rangefinder device and the golf target; and (iii) a rangefinder display; and (b) a portable computing device comprising a processor in electronic communication with the rangefinder device, a memory, and a display, the processor configured to: (A) receive or obtain the line-of-sight distance and angle of elevation (θ) to the golf target from the rangefinder device; (B) derive horizontal distance (x) and an elevation (y) of the golf target relative to the position of the golf shot, using the line-of-sight distance and angle of elevation (θ) determined by the rangefinder device, to calculate an x-coordinate position ($x_t$) and a y-coordinate position ($y_t$) for the golf target; (C) retrieve, from either the memory or from one or more data sources accessible via the Internet, accumulated shot data associated with one or more golf clubs of a golfer, the shot data comprising an average shot distance ($\bar{x}$) and golf ball launch data, the golf ball launch data comprising an initial ball speed, initial backspin rate, and launch angle; (D) select one or more of the golf clubs having the accumulated shot data; (E) predict a personalized trajectory a for golf shot taken using each of the one or more selected golf clubs, by performing at least one discretized mathematical approximation, wherein the at least one mathematical approximation utilizes the golf ball launch data for each of the one or more selected golf clubs to determine an x-position, a y-position, a velocity, and an angle-of-flight (φ) relative to the x-axis, at a plurality of discretized points along the predicted personalized trajectory; (F) compare the predicted personalized trajectory for each of the one or more selected golf clubs with the calculated $x_t$ and $y_t$ for the golf target; (G) choose a golf club from among the one or more selected golf clubs, wherein the chosen golf club has a point (x',y') along its predicted personalized trajectory in which when y' is equal to $y_t$, x' is greater or equal to $x_t$; (H) calculate a personalized AYR by applying the formula, $$AYR = \bar{x} \cdot \left(\frac{x_t}{x'}\right),$$

for the chosen golf club; and (I) indicate the personalized AYR on at least one display selected from the group consisting of the portable computing device display and the rangefinder display. In further embodiments, golf club chosen for determining the personalized AYR is indicated on the display.

In various embodiments, the processor can retrieve the golfer's golf ball launch data from a memory within the portable computing device or from one or more data sources, including but not limited to the Internet.

In various embodiments, the rangefinder device and the portable computing device are tethered together by a wired connection. In other embodiments, the rangefinder device is wirelessly recognized or paired with the portable computing device, according to a communication protocol selected from the group consisting of the BlueTooth® communication protocol, Zigbee® communication protocol, and the Wi-Fi® communication protocol.

Non-limiting examples of portable computing devices can include such electronic devices as mobile phones, tablets, laptops, wristbands, watches, belt clips, augmented reality glasses, and computer workstations associated with a movable cart. In various embodiments, the portable computing device is a mobile phone, and one or more of the steps in any of the methods for providing an AYR described herein are performed using mobile application software configured for the phone's operating system, non-limiting examples of which are Android and Apple iOS.

In another aspect, a personalized AYR can be provided using only a portable computing device comprising a display and a processor, without the need of a rangefinder. In various embodiments, the personalized AYR can be provided using application software installed on a mobile phone. Such methods can comprise the following steps: (a) retrieving course data from either a memory within the portable computing device or one or more data sources; (b) determining a horizontal distance (x) and an elevation (y) of a golf target relative to a location of the golf shot, to calculate an x-coordinate position ($x_t$) and a y-coordinate position ($y_t$) for the golf target; (c) retrieving the golfer's shot data associated with one or more golf clubs, the shot data comprising an average shot distance ($\bar{x}$) and golf ball launch data, the golf ball launch data comprising an initial ball speed, initial backspin rate, and launch angle; (d) predicting a personalized trajectory a for golf shot taken using each of the one or more selected golf clubs, by performing at least one mathematical approximation, wherein the at least one mathematical approximation utilizes the golf ball launch data for each of the one or more selected golf clubs to determine an x-position, a y-position, a velocity, and an angle-of-flight (φ) relative to the x-axis, at a plurality of discretized points along the predicted personalized trajectory; (e) comparing the predicted personalized trajectory for each of the one or more selected golf clubs with the calculated $x_t$ and $y_t$ for the golf target; (f) choosing a golf club from among the one or more selected golf clubs, wherein the chosen golf club has a point (x',y') along its predicted personalized trajectory in which when y' is equal to $y_t$, x' is greater or equal to $x_t$; (g) calculating a personalized AYR by applying the formula, $$AYR = \bar{x} \cdot \left(\frac{x_t}{x'}\right),$$

for the chosen golf club; and (h) indicating the personalized AYR on the display. In various embodiments, the horizontal distance and elevation of the golf target relative to the golfer can be determined by the GPS location of the golfer and/or the target, in combination with information from the course data regarding the terrain of the golf hole. In various embodiments, the golf target can be selected on the portable computing device display, prior to determining a personalized trajectory. In various embodiments, upon selecting a new golf target on the display, a new personalized trajectory is predicted.

In another aspect, a personalized AYR can be provided using only a rangefinder device, wherein the rangefinder device comprises: (a) an a range sensor for determining a line-of-sight distance between the device and a golf target; (b) an angle sensor for determining an angle of elevation between the rangefinder device and the golf target; (c) a display; (d) a memory; and (e) a processor configured to: (i) retrieve the line-of-sight distance and angle of elevation (θ) to the golf target from the range sensor; (ii) determine a horizontal distance (x) and an elevation (y) of a golf target relative to a location of the golf shot, to calculate an x-coordinate position ($x_t$) and a y-coordinate position ($y_t$) for the golf target; (iii) retrieve from the memory the golfer's shot data associated with one or more golf clubs, the shot data comprising an average shot distance ($\bar{x}$) and golf ball launch data, the golf ball launch data comprising an initial ball speed, initial backspin rate, and launch angle; (iv) predict a personalized trajectory a for golf shot taken using each of the one or more selected golf clubs, by performing at least one mathematical approximation, wherein the at least one mathematical approximation utilizes the golf ball launch data for each of the one or more selected golf clubs to determine an x-position, a y-position, a velocity, and an angle-of-flight (φ) relative to the x-axis, at a plurality of discretized points along the predicted personalized trajectory; (v) compare the predicted personalized trajectory for each of the one or more selected golf clubs with the calculated $x_t$ and $y_t$ for the golf target; (vi) choose a golf club from among the one or more selected golf clubs, wherein the chosen golf club has a point (x',y') along its predicted personalized trajectory in which when y' is equal to $y_t$, x' is greater or equal to $x_t$; (vii) calculate a personalized AYR by applying the formula, $$AYR = \bar{x} \cdot \left(\frac{x_t}{x'}\right),$$

for the chosen golf club; and (H) indicate the AYR on the display. In various embodiments, the processor is further configured to indicate the selected golf club on the display.

In various embodiments, and according to any of the methods, systems, or devices above, a golfer's shot data, including their average shot distance, $\bar{x}$, and golf ball launch data associated with each club, can be determined prior to a round of golf, using any means known in the art, particularly, in one non-limiting example, a launch monitor, which typically uses a high-speed camera system to determine the ball speed, spin rate, and launch angle immediately after striking the golf ball. Non-limiting examples of additional golf ball launch data that can be measured using a launch monitor and utilized to predict a personalized trajectory can include one or more of the following: backspin, side spin, total spin, spin-tilt axis, azimuth, clubhead speed, angle of attack, club path, club face angle relative to the target and/or the club path, club lie angle at impact, smash factor, dynamic loft, clubhead closure rate, impact position, and F-axis. In various embodiments, the golf ball launch data for a particular golf club represents the average value from two or more golf shots taken from the same club. In various embodiments, golf ball launch data is accumulated for a single golf club. In various embodiments, golf ball launch data is accumulated for multiple clubs, including and up to all of the clubs within the golfer's bag during a particular round.

In various embodiments, the golf ball launch data can be estimated in the absence of actual golf ball launch data from a launch monitor, based on responses given by the golfer to a survey prior to using any of the methods, systems, or devices above. Non-limiting examples can include: the golfer's age, gender, height, weight, and/or physical fitness; clubhead and/or ball speed for one or more clubs; average carry distance for one or more clubs; average dispersion off-line for one or more clubs; shape of typical ball flight (e.g. hook, draw, straight, fade, slice); height of typical ball flight (e.g. high, medium, low); location of home course; and golf handicap.

In various embodiments, the golf ball launch data can be associated with a golfer's equipment data, which can include but is not limited to: the club type, club brand, club model, loft, lie angle, shaft type, shaft brand, shaft model, shaft flex, shaft length, golf ball brand, golf ball model, golf ball type, and clubhead configuration (draw/fade/high/low).

In various embodiments, and according to any of the methods, systems, or devices above, the golf target is at least a portion of a golf course, preferably at least a portion of a golf green, and more preferably a portion of a pin positions on the golf green.

In various embodiments, either a rangefinder device or a portable computing device according to any of the methods or systems described above can further include or be associated with: one or more sensors selected from the group comprising an inclinometer, a GPS receiver, a temperature sensor, a humidity sensor, an altimeter, an anemometer, a compass, and a barometer. A processor within a rangefinder or portable computing device can be configured to retrieve environmental data from the one or more sensors or one or more data sources, the environmental data selected from the group consisting of: wind speed, wind direction, temperature, humidity, altitude, barometric pressure, previous weather conditions (e.g., the previous day, week, month) including for example precipitation influencing ground conditions, luminosity, length of day, sun angle, time of sunset, time of sunrise, shadows, solar reflection, and/or time of year, including combinations thereof. In various embodiments, environmental data is utilized in the mathematical approximation for predicting each personalized trajectory. In various embodiments, the environmental data can be displayed on the rangefinder or personal computing device display.

In various embodiments, the discretized mathematical approximation is a non-polynomial temporal discretization, which can be used to predict the personalized trajectory by simulating one or more equations in both space and time, as well as provide solutions in which the position varies as a function of time. Each term is integrated within different equations over a time step (Δt). Time steps can be conducted over any interval, based on the capabilities of the processor. In various embodiments, each term is integrated over a time step of at least about 0.01 seconds, and up to about 1 second. In various embodiments, each term is integrated over a time step of about 0.1 seconds. In various embodiments, each term is integrated over a time step of about 0.2 seconds. In various embodiments, each term is integrated over a time step of about 0.5 seconds. In various embodiments, the non-polynomial temporal discretization can be used to simulate the golf ball's x-position, y-position, velocity, and angle at each of time step. In the initial step, position of the golf ball is assumed to be traveling from (0,0) on an x,y-coordinate axis, and the velocity and angle are retrieved from the golfer's actual or estimated golf ball launch data. Non-limiting examples of non-polynomial, temporal discretization methods include, but are not limited to, explicit schemes, implicit schemes, Crank-Nicolson schemes, Euler methods, Lax-Wendroff Methods, and Runge-Kutta methods. In various embodiments, the personalized predicted trajectory can be determined using a 4th-order Runge-Kutta method.

In various embodiments, a finite-differences method approximation can be used to predict the personalized trajectory by approximating the derivatives of one or more equations, and providing solutions discretized over a spatial domain and (optionally) time intervals. As with the non-polynomial discretization, each term can be differentiated over any interval, based on the capabilities of the processor, for example at least 0.01 second, and up to 1 second, and can be used to simulated the golf ball's x-position, y-position, velocity, and angle at each of time step. In the initial step, position of the golf ball is assumed to be traveling from (0,0) on an x,y-coordinate axis, and the velocity and angle are retrieved from the golfer's actual or estimated golf ball launch data. Non-limiting examples of finite-difference approximation methods can be selected from the group consisting of a forward difference, a backward difference, a central difference, a Taylor series expansion, a Brent's method approximation, and combinations thereof.

In various embodiments, the AYR can be provided as a range of expected distances. In various embodiments, the range can be given based on a fixed distance from the AYR, such as, in a non-limiting example, 150+/−10 yards. In various embodiments, the range can be given based on a fixed percentage of the AYR, such as, in a non-limiting example, 150+/−10% (135-165 yards). In various embodiments, the range can be given based on one or more standard deviations, σ, associated with the average shot distance, $\bar{x}$, of each golf club. The standard deviation for the average distance for a particular club can be determined based on data accumulated by a launch monitor, based on actual golf shots measured over time, or can be estimated, such as, in a non-limiting example, by the golfer's handicap.

In various embodiments, the range of expected distances can be calculated from a series of predicted personalized trajectories for a low-, medium-, of high ball flight with the same club. In one non-limiting example, the range of low-, medium-, or high ball flights can be determined automatically by the processor, based on the golfer's standard ball flight with a particular club. In another non-limiting example, the golfer can select whether he or she wants to hit a lower or higher shot than normal, in order to avoid an obstacle, such as a tree.

These and other embodiments of the present invention will be apparent to one of ordinary skill in the art from the following detailed description.

Figure 1:
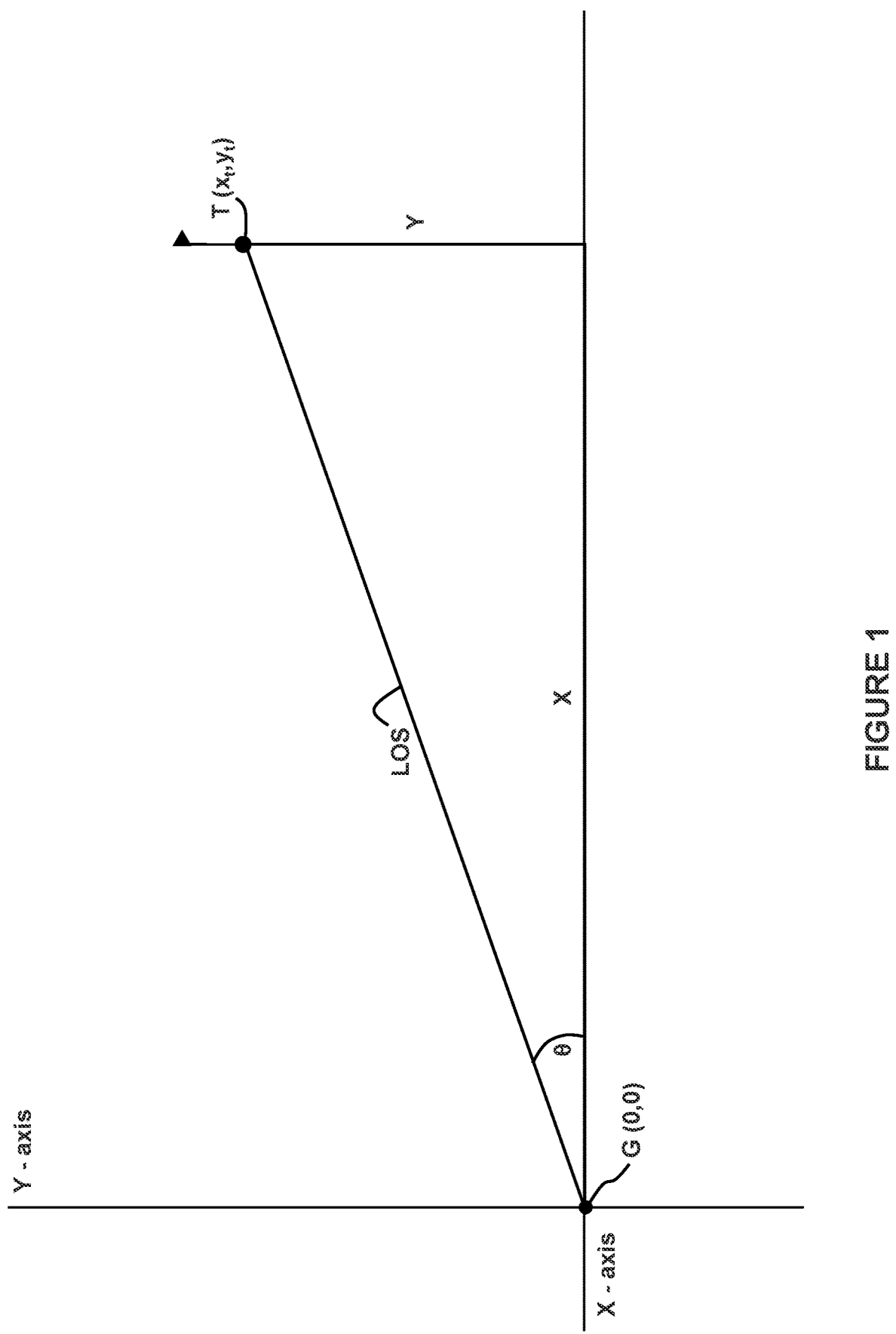
FIG. 1 illustrates the use of the line of site distance and angle to generate the horizontal distance and elevation to an uphill golf target.

The drawing figures do not limit the present invention to the specific embodiments disclosed and described herein. The drawings are not necessarily to scale, and are instead intended to clearly emphasize the principles of the invention.

DETAILED DESCRIPTION OF THE INVENTION

Definitions

As used herein, the term, "and/or" when used in the context of a listing of entities, means the entities being present singly or in combination. Thus, for example, the phrase "A, B, C, and/or D" includes A, B, C, and D individually, but also includes any and all combinations and sub-combinations of A, B, C, and D.

As used herein, the term, "angle of attack," refers to the descending or ascending path of the club-head, measured in degrees relative to horizontal.

As used herein, the term, "azimuth," also known as "side angle" or "deviation angle", is the initial horizontal angle of the golf ball relative to the target line.

As used herein, the term, "back spin," refers to the component of total spin that defines a golf ball's trajectory and lift, according to the Magnus effect.

As used herein, the term, "ball speed," refers to the measurement of a golf ball's velocity. An "initial ball speed" refers to the golf ball's velocity just after impact. Ball speed is a primary factor in generating distance.

As used herein, the term, "closure rate," refers to the rotation of the club from heel to toe measured around the shaft, commonly in degrees per second or revolutions per minute.

As used herein, the term "club path," refers to the swing path measured in a horizontal plane relative to the target line.

As used herein, the terms "club speed" or "clubhead speed" refer to the velocity of the club head measured just prior to ball contact.

As used herein, the terms "efficiency" or "smash factor" refer to the ratio between the clubhead speed and ball speed to determine the quality of the ball strike, generally expressed as ball speed divided by clubhead speed.

As used herein, the terms "embodiments of the invention," "embodiments," or "invention" do not require that all embodiments of the invention include the discussed feature, advantage, or mode of operation.

As used herein, the term, "F-axis" refers to the perpendicular axis measured relative to the directional path the golf ball rolls or slides up the clubface.

As used herein, the terms, "face angle" or "yaw" refer to the dynamic measurement (in degrees) of the club head's face plane position at a right angle 90 degrees perpendicular relative to the target line or swing path.

As used herein, the term, "face to path" refers to the face angle relative to the club path. Face to path is a primary determinant in generating side spin and curvature of the golf ball during flight.

As used herein, the term, "face to target" refers to the face angle relative to the target line at impact.

As used herein, the term, "impact location" refers to the measurement, typically in millimeters, of the contact point of the golf ball on the clubface relative to the face center. Making contact either to the side and/or above or below the center of the clubface can impact both the distance and direction of a particular shot.

As used herein, the term, "launch angle" refers to the initial vertical angle of ascent relative to the ground plane, measured in degrees. The launch angle, combined with ball spin and ball speed, are the three main components for determining ball carry and total distance.

As used herein, the terms, "lie" or "roll," with respect to a clubhead, refers to the dynamic measurement, in degrees, of the club head's face plane position horizontally relative to the ground plane. As used herein, the term, "lie," can also refer the position of a golf ball at rest prior to a golf shot, characterized by the type of ground (non-limiting examples including a tee or tee box, fairway, rough, green, sand, native area, or pine straw) and/or the condition of the ball within a particular type of ground (non-limiting examples include a "buried" lie, a "flyer" lie, or a sloped lie), which can impact both the distance and direction of a particular shot.

As used herein, the term, "loft" refers to the measurement, in degrees, of the clubhead's face plane position vertically relative to the ground plane of a club at rest on flat ground. The terms "dynamic loft" or "pitch" refer to the measurement of the clubhead's face plane position vertically relative to the ground plane at impact.

As used herein, the term, "side spin," refers to a component of the total spin that defines the ball curvature or shot shape, and is related to the spin-tilt axis.

As used herein, the term, "spin-tilt axis" refers to the axis that the golf ball rotates around to create shot curvature and lift. When the spin-tilt axis is oriented to the left (looking down range of the shot), the ball's trajectory will move from right to left. When the spin-tilt axis is oriented to the left (looking down range of the shot), the ball's trajectory will move from left to right.

As used herein, the term, "total spin" refers to the total amount of spin around the tilt axis that creates curvature and lift.

Many of the embodiments described herein are described in terms of sequences of method steps to be performed by, for example, elements of a computing device. It should be recognized by those skilled in the art that the various method steps described herein can be performed by specific circuits (e.g., application specific integrated circuits (ASICs)) and/or by program instructions executed by at least one processor. Additionally, the sequence of actions described herein can be embodied entirely within any form of non-transitory computer-readable storage medium such that execution of the sequence of actions enables the processor to perform the functionality described herein. Thus, the various aspects of the present invention may be embodied in a number of different forms, all of which have been contemplated to be within the scope of the claimed subject matter. In addition, for each of the embodiments described herein, the corresponding form of any such embodiments may be described herein as, for example, "a processor configured to" perform the described action.

Embodiments of the Invention

The present invention provides methods, devices, and systems for determining a personalized, adjusted yardage recommendation (AYR) for a golfer trying to hit a golf ball to a golf target, using a series of mathematical approximations to predict one or more non-polynomial trajectories unique to the golfer, based on the golfer's golf ball launch data, equipment, and/or environmental conditions. An AYR can be provided on a shot-by-shot basis, and in some embodiments, can additionally utilize a user's personal performance history, weather conditions, elevation, and/or golf course features.

In some embodiments, an AYR can be determined according to the following steps: (a) determining a horizontal distance, x, and an elevation, y, of a golf target relative to the golfer, to calculate an x,y-coordinate position for the golf target; (b) retrieving the golfer's golf ball launch data for one or more golf clubs, the golf ball launch data comprising at least one of the golf ball model, initial ball speed, initial spin rate, launch angle, and the average shot distance, x, associated with each golf club; (c) performing at least one mathematical approximation of the golf ball launch data to predict a personalized trajectory for a golf shot using one or more of the golf clubs; (d) comparing each predicted personalized trajectory with the golf target's x,y-coordinate position; (e) selecting a golf club having a predicted personalized trajectory that has a point (x',y') such that when y' is equal to y, x' is greater or equal to x; and (f) calculating an AYR, by applying the formula, $$AYR = \bar{x} \cdot \left(\frac{x_t}{x'}\right).$$

Figure 2:
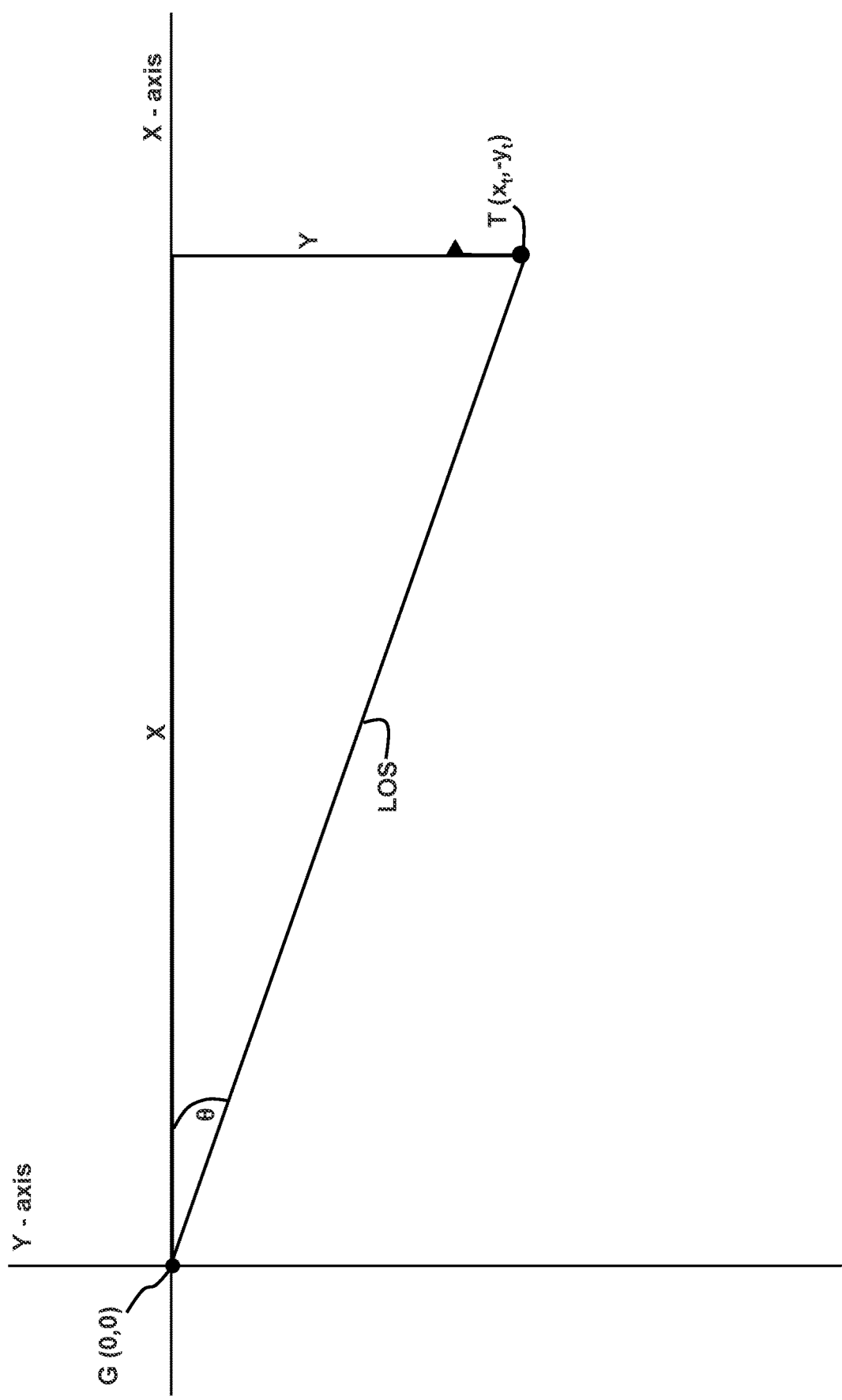
FIG. 2 illustrates the use of the line of site distance and angle to generate the horizontal distance and elevation to a downhill golf target.

In two dimensions, the horizontal distance, x, and the elevation, y, of the golf target, T, can form a right triangle, where the hypotenuse of the triangle is the line-of-sight (LOS) distance between the golfer and the golf target, as shown in FIG. 1. In an x,y-coordinate system, the golf target, T, is at a point $(x_t, y_t)$, whereas the golfer, G, is at point (0,0). In situations in which the golf target, T, is below the golfer, the target is at the point $(x_t, -y_t)$ in an x,y-coordinate system, as shown in FIG. 2.

In some embodiments, the LOS can be determined using a rangefinder device with special features and capabilities for use when golfing. Such rangefinders utilize sonar, radar, or laser reflectometry to determine the distance to a target. In particular, laser-based rangefinders typically calculate a range by emitting laser pulses to the target and measuring the time it takes for the reflection to return to the rangefinder. Suitable rangefinders for determining the LOS distance to the target are well known in the art.

However, a golfer rarely encounters a golf shot where the target is exactly level, i.e. where the golf target is at a point y=0 and x≠0. As a result, some rangefinders provide a secondary distance to the target which accounts for the difference in elevation between the golf target and the golfer. Methods by which the secondary distance is calculated is described in further detail below. Generally, such rangefinders comprise an angle sensor, also called an "inclinometer" or "tilt sensor", which measures an angle of elevation to the golf target. The horizontal distance and elevation can then be calculated using geometry, where the horizontal distance can be derived by multiplying the LOS distance by the cosine of the angle of elevation (θ), and the elevation can be derived by multiplying the LOS distance by the sine of the angle of elevation θ.

Figure 3:
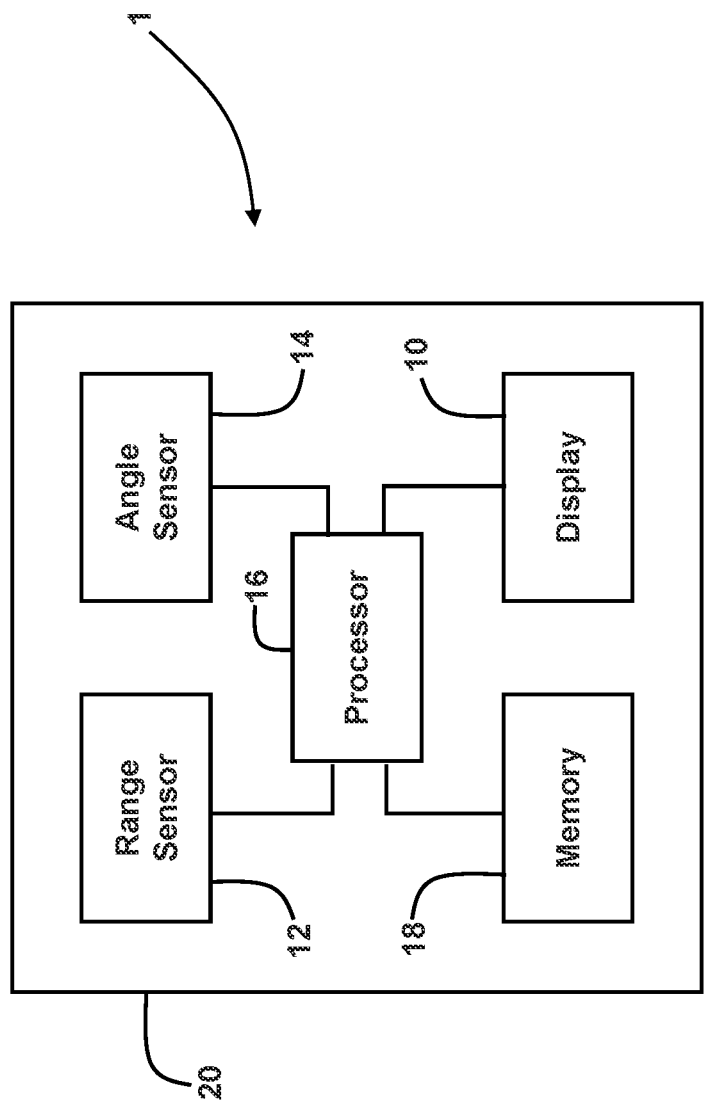
FIG. 3 is a block diagram illustrating exemplary components of a range finder device that can be used in accordance with the principles of the present invention.
Figure 4:
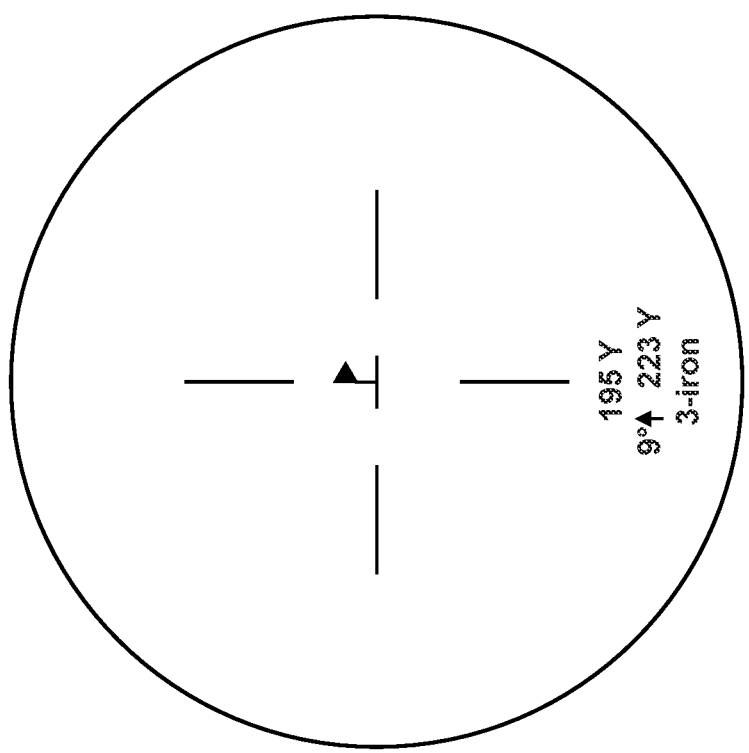
FIG. 4 illustrates an exemplary schematic view of a golf target observed through the display of a rangefinder device, indicating the horizontal distance, adjusted yardage, and club recommendation to a golfer.

A non-limiting example of a rangefinder device, illustrated as 1 in the schematic shown in FIG. 3, contains a processor 16 coupled with: a display 10 for selecting a golf target and indicating the LOS distance and other information, non-limiting examples of which include one or more secondary distances, environmental conditions, course condition, and/or recommended golf club(s); a range sensor 12, which measures the distance to a target, for example, by sonar, radar, or laser reflectometry; an angle sensor 14; a memory 18 for storing data such as a computer program to control the functionality of the device 200; and a portable handheld housing 20 for housing the display 10, range sensor 12, the angle sensor 14, the processor 16, and the memory 18. Each of these components are described in detail in U.S. Pat. Nos. 7,329,377 and 8,314,923, herein incorporated by reference in their entireties. An example view of a rangefinder display 10 when using a laser rangefinder device 1 to determine the range to a golf target is illustrated in FIG. 4. In FIG. 4, a golf flag, representing the golf target, is situated within a reticle, while the LOS distance, angle of elevation, secondary distance, and club recommendation are provided at the bottom of the display.

Accordingly, in another embodiment, the method step of determining the horizontal distance, x, and the elevation y, of the golf target can be performed by determining an LOS distance and angle of elevation between the golfer and a golf target, using a rangefinder device comprising a range sensor, an angle sensor; and subsequently calculating the horizontal distance and elevation from the LOS distance and angle of elevation, as described above. In a further embodiment, the range sensor is a laser range sensor that uses laser reflectometry.

In another embodiment, the rangefinder device can further optionally include, or be able to communicate with, a GPS receiver, which can determine the location of the device and a golf target in terms of latitude, longitude, and elevation, and is particularly useful when the golf target is a flag on a green that is obscured or blocked by a tree, hill, or other natural or man-made feature on the golf course. In another embodiment, the rangefinder device and/or GPS receiver may include an altimeter to provide altitude readings. In another embodiment, one or more golf targets for a particular golf hole are stored within the memory, including but not limited to: the front, middle, and/or back of the green; hazards; course boundaries; and/or other natural or man-made course features. In another embodiment, the user can select a golf target at any position on the golf hole, such as on the display of a personal computing device in which the GPS receiver is located.

In another embodiment, the horizontal distance and elevation of the golf target relative to the golfer can be transmitted to, or determined by, a portable computing device that includes one or more non-transitory computer-readable media for storing computer-executable instructions, code, or software. Non-limiting examples of portable computing devices include mobile phones, tablets, laptops, wristbands, watches, belt clips, augmented reality glasses, and computer workstations associated with a movable cart. In another embodiment, the portable computing device is a mobile phone. In further embodiments, one or more steps of any of the methods disclosed herein are performed using the mobile phone. In other embodiments, all of the steps of any of the methods disclosed herein are performed using the mobile phone.

In another embodiment, the portable computing device can contain applications or software for performing one or more of the steps in any of the methods disclosed herein, designed for use with one or more operating systems, non-limiting examples of which include Apple® OS X or macOS, Linux™, and any one of a number of Microsoft® Windows® operating systems, such as the currently active families of Windows® NT and Windows® Embedded, which encompass the subfamilies of Windows® Embedded Compact (Windows® CE) and/or Windows® Server. Non-limiting examples of operating systems utilized by phones, tablets, and other mobile devices generally include, but are not necessarily limited to, Android, Android Oreo, and Apple® iOS.

Non-transitory computer-readable media may include, but are not limited to, one or more types of hardware memory, non-transitory tangible media (for example, one or more magnetic storage disks, one or more optical disks, one or more flash drives), and the like. For example, a memory included in the electronic device may store computer-readable and computer-executable instructions or software for implementing performing one or more of the steps of any of the methods described herein for determining and providing an AYR. In another embodiment, the memory may include a computer system memory or random-access memory, non-limiting examples include DRAM, SRAM, EDO RAM, and others. The memory may include other types of memory as well, or combinations thereof. In another embodiment, the portable computing device also includes one or more configurable and/or programmable processing devices, for example, processors and associated cores.

In another embodiment, the rangefinder device can further comprise an external device interface that allows for electronic communication with the portable computing device. The external device interface preferably provides an industry standard interface, such as a wireless or wired connection. In the case of a wired connection, a data bus may be provided using any protocol, such as Advanced Technology Attachment (ATA), Personal Computer Memory Card International Association (PCMCIA), DisplayPort, Mini DisplayPort, High-Definition Multimedia Interface (HDMI®), Digital Visual Interface (DVI), Micro-DVI, Mini-DVI, Lightning®, Thunderbolt®, Universal Serial Bus (USB), MicroUSB, and/or USB-C®, as non-limiting examples. A wireless connection may use low powered electromagnetic waves to transmit data using any wireless communication protocol, such as BlueTooth®, Zigbee®, Wi-Fi®, or IEEE 802.11, as non-limiting examples.

In another embodiment, a golfer may interact with the portable computing device through a visual display device, such as a touch screen, which may display one or more graphical user interfaces that render upon execution of the computer readable instructions, code, or application software. The electronic device may include other I/O devices for receiving input from a user, for example, a keyboard (virtual or physical) or any suitable multi-point touch interface, a pointing device (for example, a mouse or stylus), a microphone, and/or an image capturing device (e.g., a camera or scanner). The computing device may include other suitable conventional I/O peripherals.

In another embodiment, the golfer can save his or her golf ball launch data into the memory of the rangefinder device and/or portable computing device, for use in predicting a personalized trajectory, and ultimately, generating an AYR. In another embodiment, the golfer can input the golf ball launch data into the portable computing device for storage within the device memory, using any of the visual display or input devices described above. In another embodiment, the golf ball launch data can subsequently be transferred from the portable computing device to the rangefinder device, either through a wired or wireless connection, as described above. In another embodiment, the processor within the rangefinder device and/or portable computer device can be programmed to retrieve the golfer's golf ball launch data from one or more data sources, such as the Internet.

In another embodiment, the golf ball launch data comprises at least one, and preferably all, of the following metrics: the golf ball model, initial ball speed, initial spin rate, launch angle, and the average shot distance, $\bar{x}$, associated with one or more golf clubs that a golfer has in his or her bag during a round of golf. In some embodiments, the golf ball launch data is associated with all of the clubs, except for a putter, a golfer may have in his or her bag for use during a round of golf. Other metrics that can be included within the launch data can be selected from the group consisting of: backspin, side spin, total spin, spin-tilt axis, azimuth, clubhead speed, angle of attack, club path, club face angle relative to the target and/or the club path, club lie angle at impact, smash factor, dynamic loft, clubhead closure rate, impact position, and F-axis.

In another embodiment, one or more of the metrics that comprise the golf ball launch data can be measured by a launch monitor. Such launch monitors capable of measuring one or more of the above metrics, particularly initial ball speed, initial spin rate, and launch angle are conventionally known in the art and are described in U.S. Pat. No. 7,395,696, which is herein incorporated by reference in its entirety. Generally, launch monitors utilize a high-speed, high-resolution camera system to capture a plurality of images, which are analyzed to determine the golf ball launch data. In some embodiments, a golfer hits a plurality of golf shots with one or more clubs, using a launch monitor to accumulate and analyze the golf ball launch data for each club. In further embodiments, an average and standard deviation for one or more of the metrics that comprise the golf ball launch data can be determined, in order that an average shot distance, $\bar{x}$, and a standard deviation, $\sigma$, can be determined for the one or more clubs.

In another embodiment, the launch monitor can be associated with any of the wired or wireless network connections described above, for transmitting the golf ball launch data to either or both of a portable computing device and a rangefinder device. In some embodiments, the golfer's golf ball launch data is transmitted from a launch monitor to a portable computing device, the personalized trajectories are predicted using mathematical approximations performed on the portable computing device, and the resulting AYR is communicated to the golfer through the rangefinder device, a display on the portable computing device, or both.

In another embodiment, when a golfer is unable to collect his or her golf ball launch data using a launch monitor, one or more of the metrics can be estimated based on the golfer's responses to a series of personal profile questions regarding the golfer's age, ability, and physical characteristics. The personal profile questions can be answered either within the software, such as a mobile application, on the portable computing device itself, or via the Internet. Generally, a golfer will access the questions during initial product or account registration, although the golfer can provide new responses at any time, either as more information is accumulated or to update previous responses. Information about the golfer that can be acquired by the golfer's responses to the personal profile questions can include, but are not limited to: the golfer's age, gender, height, weight, and/or physical fitness; clubhead and/or ball speed for one or more clubs, e.g. a driver clubhead speed; average carry distance for one or more clubs; average dispersion off-line for one or more clubs; shape of typical ball flight (e.g. hook, draw, straight, fade, slice); height of typical ball flight (e.g. high, medium, low); location of home course; and golf handicap.

In another embodiment, the golf ball launch data, predicted trajectories, and/or AYRs from a plurality of golfers can be compiled into a database and utilized to estimate a golfer's initial ball speed, spin rate, and launch angle when their golf ball launch data is not known. For example, the golfer can provide the average carry and/or total distance and typical shot height for one or more, and preferably all, of the clubs in his or her bag. For each club, the golfer's provided distance and shot height can be compared with the distance and height of trajectories of other golfers that were predicted based on actual golf ball launch data. A trajectory that produces a similar distance and height can be selected, and the golf ball launch data used to predict that trajectory can be used for the golfer. In further embodiments, the search group can be narrowed or limited to the predicted trajectories of golfers who have a similar golf handicap, age, gender, height, weight, or other physical characteristics.

In a non-limiting example, the initial ball speed, spin rate, and launch angle of a 7-iron hit by a 36-year old male with a 15 handicap who reports that they have a high ball flight and an average 7-iron distance of 170 yards can be estimated from the golf ball launch data of one or more golfers within the database who report a similar distance and shot height.

The golfer's initial ball speed, spin rate, and launch angle can be estimated for his other clubs based on the distance(s) and height(s) provided, using a similar process. In some embodiments, a golfer can edit the average distance and shot height of one or more clubs to obtain an updated estimate of his or her golf ball launch data. In some embodiments, if a golfer with estimated golf ball launch data subsequently obtains measured golf ball launch data, e.g. by using a launch monitor, the golfer can input his actual golf ball launch data in place of the estimated data.

In another embodiment, either actual or estimated golf ball launch data can be associated with a golfer's equipment data, which can include but is not limited to: the club type, club brand, club model, loft, lie angle, shaft type, shaft brand, shaft model, shaft flex, shaft length, golf ball brand, golf ball model, golf ball type, and clubhead configuration (draw/fade/high/low).

In another embodiment, a golfer's trajectory can be predicted based on the golf ball launch data to provide a personalized AYR. As described above, several rangefinder devices and GPS-based accessories and mobile applications provide both LOS and adjusted distances to the target. In some instances, adjusted distances to the target are determined based on the theoretical trajectory of the golf ball in flight. However, these adjusted distances to the target are standardized based on the golf club, the average shot distance with that club, or the trajectory shape, if the trajectory is predicted at all. For example, the methods described in U.S. Pat. Nos. 8,529,380 and 10,682,562, above, provide recommendations based on the results of actual shots made by the golfer, but do not determine the trajectory of a golf shot to make that recommendation. Although course terrain, slope, and environmental factors such as wind can be utilized to adjust the recommendation, each of the shot results are calculated based on where the golf ball stopped, and not where it landed. Accordingly, future recommendations based on the total distance, rather than a "carry distance" (the distance the ball actually traveled in the air) may be inaccurate, particularly if one or more golf shots used for calculating the distance were mishit, hit an obstruction such as a tree, flew into a hazard, and/or purposefully hit less than a full distance with that particular club. In contrast, most golfers determine which club to hit based on the carry distance, particularly when attempting to hit the ball onto the green.

In another example, the rangefinder devices described in U.S. Pat. Nos. 7,239,377, 7,535,553, and 7,859,650, incorporated by reference in their entireties above, utilize a standardized look-up table to determine an adjusted distance based on pre-determined factors which are scaled based on the LOS distance and the angle to the target. From the LOS distance, the adjusted distance to the target is determined by adding the horizontal distance to the target, LOS×cos(θ) and the elevation to the target, LOS×sin(θ), which are equivalent to x and y in FIG. 2, above. For example, when the LOS distance to the golf target is 150 yards, and the angle of elevation, θ, is 10 degrees, the adjusted distance to the target is (150×cos(10))+(150×sin(10)), or 173.77 yards. The golfer can then select a club that he or she believes would go further than 173.77 yards if the golf target was at the same elevation as the golfer.

In another example, the rangefinder device in U.S. Pat. No. 8,314,923 utilizes user-defined distances for one or more golf clubs to predict a standardized trajectory for each club and distance. Therefore, a user-defined distance of 200 yards upon hitting a shot with a 6-iron will always have the same trajectory, regardless if one person has a relatively high trajectory and a second person has a relatively low trajectory. Further, the trajectories themselves are predicted according to the teachings of U.S. Pat. No. 7,654,029, herein incorporated by reference in its entirety, which assumes a polynomial trajectory according to the equation $T=a_0+a_1R+a_2R^2+a_3R^3\ldots$ wherein T is the trajectory, coefficients $a_0$, $a_1$, $a_2$, etc. are calculation from the angle to the target based on a series of polynomial equations having pre-determined parameters.

However, while the trajectory of a projectile can be modeled as a parabola or other polynomial equation, such models neglect the effect of forces other than gravity. Instead, such factors as wind, drag, and changes in altitude or humidity can also affect the flight of a golf ball. In particular, when a ball is struck with backspin, the pressure around the ball changes, affecting its flight. This phenomenon, called the "Magnus effect," directs air upwards in front of the ball and downwards behind it, causing the ball to gain loft and have a longer ball flight as a result of the pressure difference that was created. The Magnus force lifting the ball is caused by the rotation and velocity of the golf ball. The rotation causes air disturbances perpendicular to the direction of the angular velocity, causing the direction of flight to be altered perpendicular to the linear velocity.

Figure 5:
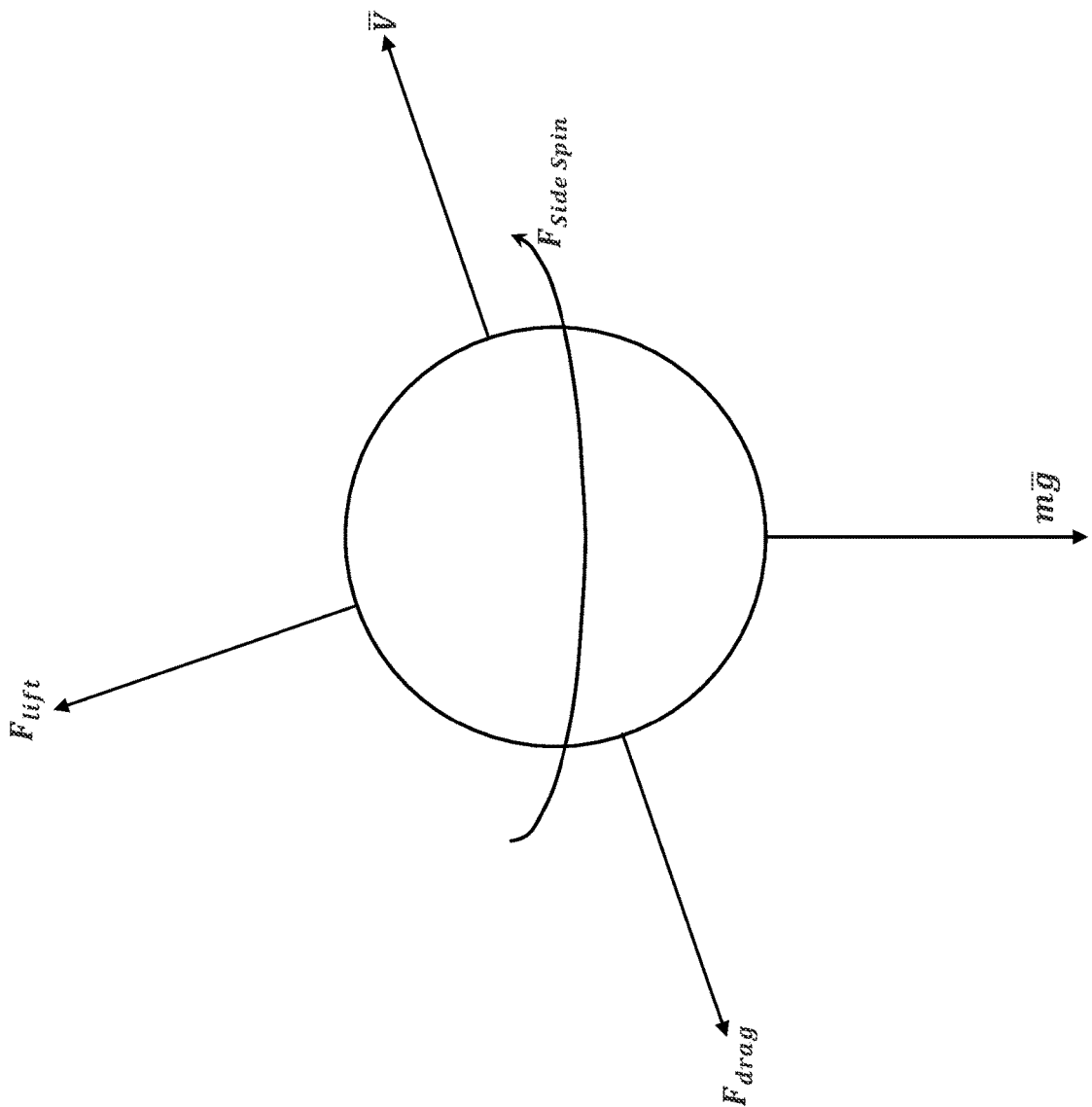
FIG. 5 illustrates the various forces that act upon a golf ball during flight.

A diagram of the effect of the Magnus force, as well as drag, side spin, and gravity, on a golf ball in flight is shown in FIG. 5. As shown, the unit vector of the golf ball's velocity is shown as $\vec{V}$; the Magnus Force is shown as $F_{lift}$; the drag force, equal in magnitude but in the opposite direction of the motion of the ball, is shown as $F_{drag}$; the side spin of the ball is shown as $F_{sidespin}$; and the gravitational force is shown as $m\vec{g}$. Furthermore, because the golf ball has dimples, the air around the golf ball is turbulent and close to the surface, reducing the rate of deceleration and dramatically increasing the Magnus effect. Because the number, size, shape, and depth of dimples is not uniform from manufacturer to manufacturer or even from model to model within the same manufacturer, in another embodiment, a golfer can input his or her golf ball model prior to a personalized AYR being made. In some embodiments, the golfer inputs a golf ball model prior to a round a golf, and each AYR is made based on that golf ball model. In some embodiments, the golfer inputs a golf ball model each time he or she switches golf balls during around, to provide the most accurate AYR.

As a result, classical physical models are inadequate to simultaneously account for the Magnus force, drag, side spin, gravity, and other atmospheric conditions on the golf ball. Instead, and in another embodiment, mathematical modeling of terms that define a golf ball's trajectory can be performed using a series of non-linear ordinary and partial differential equations. While exact solutions to many non-linear ordinary and partial differential equations often cannot be solved symbolically, several numerical methods have been applied to obtain approximate solutions that are often sufficient to solve practical scientific, physics, and engineering problems. Such approximations can be determined by performing a series expansion using calculus, or by using one or more linear multi-step methods or Runge-Kutta methods, either of which can be explicit or implicit methods. Non-limiting examples of implicit linear multi-step methods include Adams-Moulton methods and backwards differentiation methods, while implicit Runge-Kutta methods can include, but are not limited to, diagonally implicit Runge-Kutta method, singly diagonally implicit Runge-Kutta methods, and Gauss-Radau methods. Non limiting examples of explicit methods include the linear multi-step Adams-Bashforth methods and explicit Runge-Kutta methods having a lower diagonal Butcher tableau. Other methods that can be utilized include finite difference approximation methods, Taylor series expansions, Brent's method, Euler and backward Euler methods, first-order exponential integrator methods, variable order methods (such as those based on Richardson extrapolation), multiderivative methods (such as the Parker-Sochacki or Bychkov-Scherbackov methods), Nystrom methods, geometric integration methods, Crank-Nicolson schemes, Lax-Wendroff methods, and piecewise analytic methods. Those skilled in the art would appreciate that the above list of numerical methods to solve non-linear ordinary and partial differential equations is non-exhaustive, and that others have been omitted for clarity.

When attempting to approximate the movement of an object, such as a golf ball, continuous functions, variables, and equations can be discretized into separate counterparts in both space and/or time. Finding solutions to each counterpart generally involves the differentiation or integration of every term in each equation as a solution interval, t, divided into subintervals having a step-size ($\Delta t$). In some embodiments, with respect to the trajectory of a golf ball, the solution interval, t, can be determined by the time the ball is in flight after it is struck (at $t_0$) until the ball lands. Generally, depending on the type of club used, the top of shot played, and the atmospheric conditions in which the round is being played, a golf ball's flight can range from less than one second and up to ten or more seconds. The solutions of each equation can be determined over subintervals having any step-size ($\Delta t$) based on the capabilities of the processor in either the rangefinder device or portable computing device. In some embodiments, the step size can be at least about 0.05 seconds, about 0.1 seconds, about 0.15 seconds, about 0.20 seconds, about 0.25 seconds, about 0.3 seconds, about 0.35 seconds, about 0.4 seconds, about 0.45 seconds, about 0.5 seconds, or about 0.75 seconds, up to about 1 second. In some embodiments, the step size can be less than about 1 second, about 0.75 seconds, about 0.5 seconds, about 0.45 seconds, about 0.4 seconds, about 0.35 seconds, about 0.3 seconds, about 0.25 seconds, about 0.2 seconds, about 0.15 seconds, or about 0.1 seconds, down to about 0.05 seconds. In some embodiments, the step size can be any unit of time between and inclusive of about 0.05 seconds and about 1 seconds. In various embodiments, each term is integrated over a time step of about 0.2 seconds. In various embodiments, each term is integrated over a time step of about 0.2 seconds.

In some embodiments, the trajectory of a golf ball struck by a golfer with a defined golf club can be approximated using a non-polynomial temporal discretization, performed by any of the numerical methods described above. In some embodiments, the temporal discretization is performed using a Runge-Kutta method, particularly an explicit Runge-Kutta method, and more particularly a 4th-order Runge-Kutta method ("RK4"). In general, the Runge-Kutta family of methods uses multiple points within each subinterval (e.g., in the subinterval [$t_n, t_{n+1}$]) to approximate the value of the function at time $t_{n+1}$. An example of the RK4 method is demonstrated below. First, let an initial value problem be specified as follows.

$$\frac{dy}{dt} = f(t, y), \quad (1)$$
$$y(t_0) = y_0$$

In this example, y is an unknown function of time t, which is to be approximated. dy/dt is the rate at which y changes, and is a function of both t and y. At the initial time to, the corresponding y value is $y_0$. Upon choosing a step-size $\Delta t>0$, $y_{n+1}$ and $t_{n+1}$ can be defined by the following equations:

$$y_{n+1} = y_n + \tfrac{1}{6}\Delta t(k_1 + 2k_2 + 2k_3 + k_4) \quad (2)$$

$$t_{n+1} = t_n + \Delta t \quad (3)$$

When n=0, 1, 2, 3, . . . $k_1$, $k_2$, $k_3$, $k_4$ can be defined by the following equations:

$$k_1 = f(t_n, y_n) \quad (4)$$

$$k_2 = f\left(t_n + \frac{\Delta t}{2}, y_n + \Delta t\frac{k_1}{2}\right) \quad (5)$$

$$k_3 = f\left(t_n + \frac{\Delta t}{2}, y_n + \Delta t\frac{k_2}{2}\right) \quad (6)$$

$$k_4 = f(t_n + \Delta t, y_n + \Delta t k_3) \quad (7)$$

Figure 6:
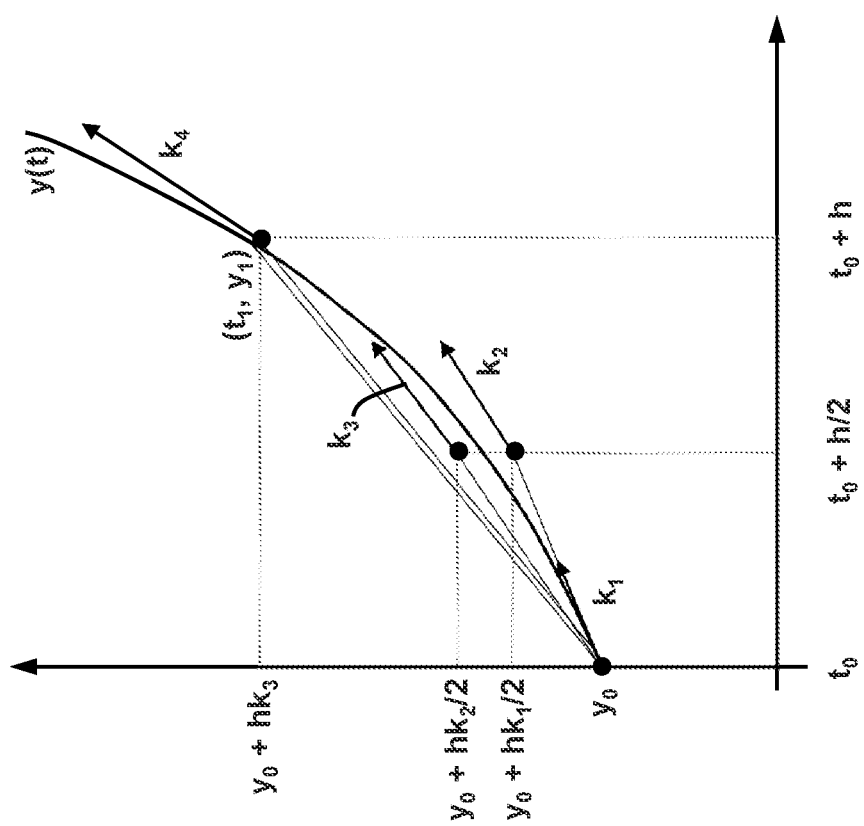
FIG. 6 illustrates the four slopes that are calculated at each interval when performing a temporal discretization using the RK4 method.

In this example, $y_{n+1}$ is the RK4 approximation of $y(t_{n+1})$, and the next value ($y_{n+1}$) is determined by the present value ($y_n$) plus the weighted average of four increments, where each increment is the product of the size of the subinterval $\Delta t$ and an estimated slope of the function at that increment. In equations (3)-(6) above, $k_1$ is the slope at the beginning of the subinterval, using y (Euler's method); $k_2$ is the slope at the midpoint of the subinterval, using y and $k_1$; $k_3$ is the slope at the midpoint of the interval, using y and $k_2$; and $k_4$ is the slope at the end of the subinterval, using y and $k_3$. In averaging the four slopes, greater weight is given to the slopes at the midpoint. A graphical representation of $k_1$, $k_2$, $k_3$, and $k_4$ determined for a function y(t) over the subinterval [$t_0, t_1$] is shown in FIG. 6.

Figure 7:
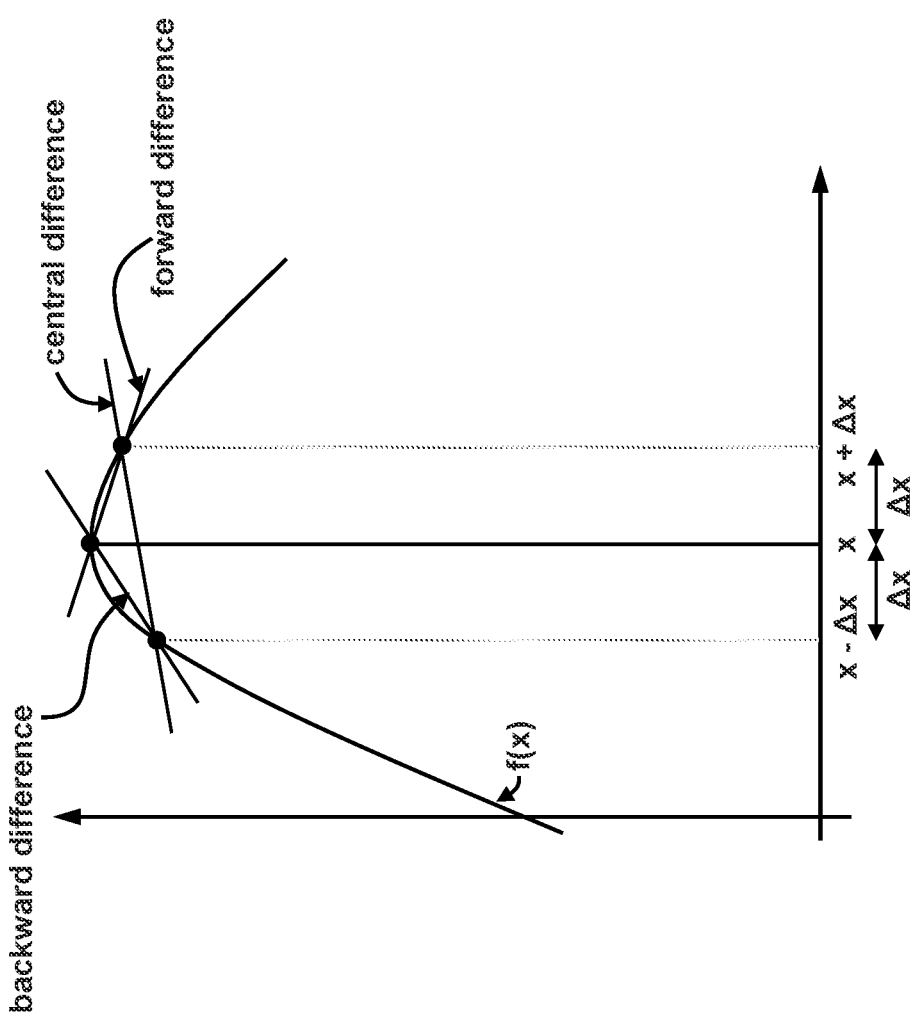
FIG. 7 illustrates the three types of finite differences that can be used to approximate the derivatives of differential equations.

In some embodiments, the trajectory of a golf ball struck by a golfer with a defined golf club can be approximated using a finite differences approximation. Finite difference methods convert derivatives present within ordinary differential equations or partial differential questions, which are typically non-linear, into a system of linear equations that approximate those derivatives and can be solved by matrix algebra. There are three basic types of finite differences: a forward difference, a backward difference, and a central difference, each of which is illustrated in FIG. 7. A forward difference is an expression of the form:

$$\Delta_h[f](x) = f(x+h) - f(x) \quad (8)$$

Depending on the application, the spacing, h, may be variable or constant. When omitted, h is understood to be 1. A backward difference uses the function values at x and x−h, instead of the values x+h and x that are used to determine the forward difference:

$$\nabla_h[f](x) = f(x) - f(x-h) \quad (9)$$

Finally, the central difference is given by:

$$\delta_h[f](x) = f\left(x + \frac{1}{2}h\right) - f\left(x - \frac{1}{2}h\right) \quad (10)$$

Each of the finite-difference approximations can be expressed as higher-order differences, which enable the determination of both higher-order methods for approximating the derivative and for higher-order derivatives. As a non-limiting example, the first order derivative of a function can be approximated in one dimension using a five-point stencil, which can be derived from the Taylor series expansion:

$$f(x \pm h) = f(x) \pm hf'(x) + \frac{h^2}{2}f''(x) \pm \frac{h^3}{6}f^3(x) + O_{1\pm}(h^4) \tag{11}$$

A five-point stencil, approximating the first derivative at point x, along with its two immediately preceding points, x−2h and x−h, and two immediately successive points, x+h and x+2h is given by the following:

$$f'(x) \approx \frac{-f(x+2h) + 8f(x+h) - 8f(x-h) + f(x-2h)}{12h} \tag{12}$$

With respect to a golf ball's trajectory, the variables that can be approximated at any point in time using any of the above-described methods, including the RK4 and finite-differences methods, can include: an x- and y-coordinate position, in which the x-axis is defined by a horizontal line extending to the golf target and the y-axis is defined by a vertical line extending from the golfer; a velocity; and an angle-of-flight φ, in the y-direction relative to the x-axis. With regards to the angle-of-flight φ, a positive value indicates that the golf ball is ascending, whereas a negative value indicates that the golf ball is descending. In some embodiments, at $t_0$, the ball is at rest at x-y coordinate position (0,0), and the velocity and angle-of-flight φ of the ball flight are equivalent to the initial ball speed and launch angle determined from the golfer's actual or estimated golf ball launch data. During the next step, $t_1$, and at each successive step, the velocity, ball flight angle-of-flight φ, and the x-y coordinate position of the golf ball can each be defined as separate functions, y(t) to be approximated at each step, $t_n$, over the entire solution interval t. In some embodiments, the golf ball's velocity at time $t_{n+1}$ can be described by the following equation:

$$y_{n+1(velocity)} = -g * \left(\frac{F_{drag}}{Weight} + \sin\varphi_n\right) \tag{13}$$

wherein g is a constant, equal to the acceleration of gravity, and can in some embodiments be expressed as 32.174 lbm ft/lbf sec² (or ft/sec²). Weight is the weight of a golf ball, which can be described in lbf, for example, 0.10125 lbf. $F_{drag}$ can be derived according to the following equation:

$$F_{drag} = C_d * q * A_{ball} \tag{14}$$

wherein $C_d$ is the drag coefficient, q is the dynamic pressure around the ball, and $A_{ball}$ is the area of the golf ball, 0.154 ft². $C_d$ can be derived from the rotational speed ratio, $\omega_r$, of the golf ball by the following equation:

$$C_d = 0.1403 - (0.3406 * \omega_r * \log \omega_r) + (0.3747 * \omega_r^{1.5}) \tag{15}$$

wherein the rotational speed ratio, $\omega_r$, is a constant, determined using the following equation:

$$\omega_r = \frac{\omega * d * \pi}{V_n} \tag{16}$$

wherein $V_n$ is the velocity in ft/s at time n, ω is the angular velocity of the backspin, in some embodiments expressed in rpm or rps, and d is the diameter of the golf ball, 0.14 ft. In equation (9), the dynamic pressure, q, can be determined using the following equation:

$$q = \frac{1}{2} * \frac{\rho}{R_{air} * T} * V_n * \frac{V_n}{g} \tag{17}$$

wherein ρ is the atmospheric pressure, $R_{air}$ is the gas constant for air, and T is the temperature. In some embodiments, ρ can be expressed in pound force per square foot (pfsa); $R_{air}$ can be expressed in $$\frac{ft * lbf}{lbm * R}$$

where R is the ideal gas constant; and T can be expressed in Rankines, Kelvin, degrees Celsius, or degrees Fahrenheit.

In some embodiments, the golf ball's angle of flight φ at time $t_{n+1}$ can be described by the following equation:

$$y_{n+1(\varphi)} = \frac{g * \left(\frac{F_{lift}}{Weight} - \cos\varphi_n\right)}{V_n} \tag{18}$$

wherein $F_{lift}$ is the Magnus force, and can be derived according to the following equation:

$$F_{lift} = C_L * q * A_{ball} \tag{19}$$

wherein $C_L$ is the lift coefficient. $C_L$ can be derived from the rotational speed ratio, $\omega_r$, of the golf ball by the following equation:

$$C_L = 0.3996 + (0.1583 * \log \omega_r) + (0.3790 * \omega_r^{-0.5}) \tag{20}$$

In some embodiments, the golf ball's x-coordinate position at time $t_{n+1}$ can be described by the following equation:

$$y_{n+1(X)} = y_{n(X)} + (V_n * \cos \varphi_n) \tag{21}$$

In some embodiments, the golf ball's y-coordinate position at time $t_{n+1}$ can be described by the following equation:

$$y_{n+1(Y)} = y_{n(Y)} + (V_n * \sin \varphi_n) \tag{22}$$

In some embodiments, a golfer's trajectory with a particular club can be predicted using the RK4 method or using the finite-differences method. In a non-limiting example, the RK4 method can be utilized to model the trajectories of a golf shots made by a golfer who was able to provide initial ball speed, backspin rate, and launch angle for five clubs, a 3-hybrid, a 4-iron, a 6-iron, 9-iron, and a pitching wedge. The temperature, relative humidity, and pressure in the space in which the golf shots were struck were 80° F., 74%, and 101.0498 kPa. The initial golf ball launch data are provided in Table 1, below.

TABLE 1

| Club | Ball Speed (mph) | Backspin Rate (rpm) | Launch Angle (degrees) |
|---|---|---|---|
| 3-hybrid | 141.06 | 3527.49 | 12.45 |
| 4-iron | 132.92 | 5135.52 | 16.38 |
| 6-iron | 127.98 | 6030.77 | 18.78 |
| 9-iron | 106.43 | 8641.92 | 23.80 |
| PW | 101.00 | 9161.03 | 26.29 |

Figure 8:
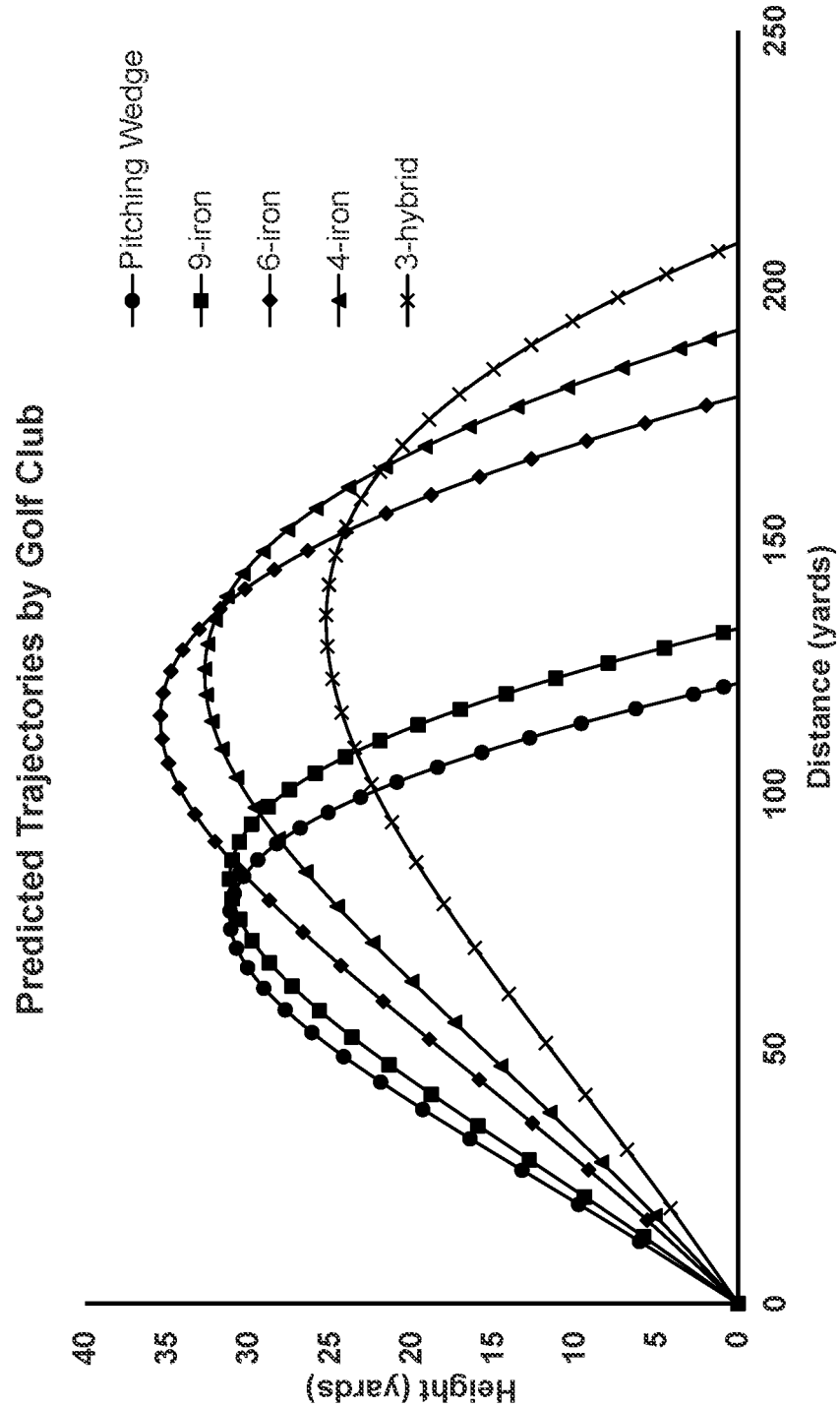
FIG. 8 illustrates the RK4-modeled trajectories predicted from a golfer's golf ball launch data, using five different golf clubs.
Figure 9:
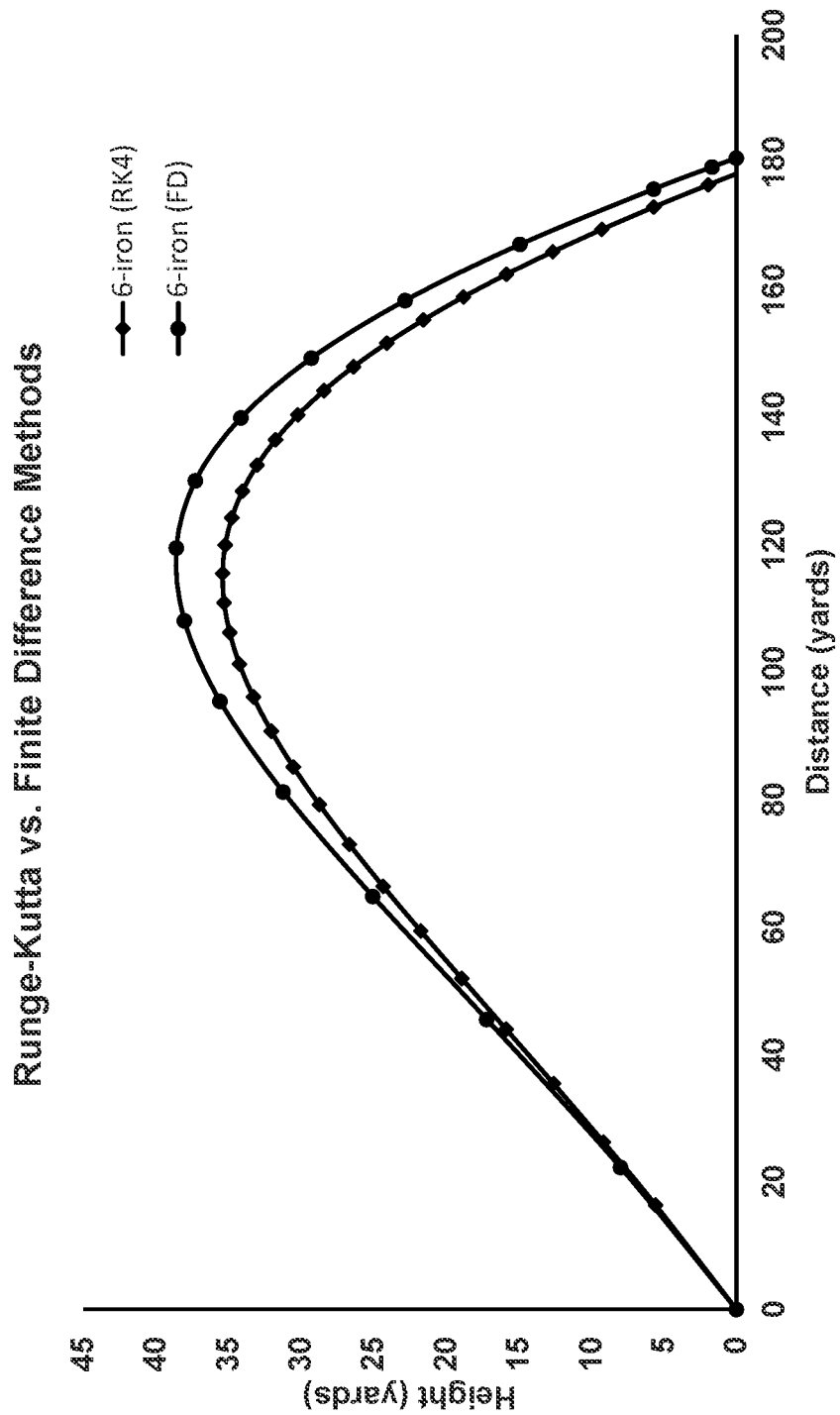
FIG. 9 illustrates a comparison of the modeled trajectories for the same golfer's 6-iron shot, using RK4 and finite-differences methods.

The golfer's modeled trajectories to golf targets at the same elevation as the golfer when using a 3-hybrid, a 4-iron, a 6-iron, 9-iron, and a pitching wedge, respectively, are illustrated in FIG. 8. Each trajectory was calculated at 0.2-second time intervals, until the y-position returned to zero (x,0). In another non-limiting example, the same golfer's trajectories modeled using a finite differences approximation using a five-point stencil in one dimension, using Brent's method, a root-finding (i.e., $f(x)=0$) algorithm which combines the bisection method, the secant method, and inverse quadratic interpolation to determine where the golf ball is projected to land. The modeled trajectory of the golfer's 6-iron, calculated using either the RK4 method or the finite-differences method, is illustrated in FIG. 9.

In some embodiments, for a shot in which the golf target is above the golfer (i.e. when y is greater or equal to zero), the velocity, angle-of-flight $\varphi$, x-coordinate position, and y-coordinate position of the golf ball can be calculated until the y-position returns to zero ([x,0]), similarly to a shot with no elevation change. In some embodiments, when the golf target is below the golfer (i.e. when y is less than zero), a modeled trajectory can be extended through the x-axis until for a pre-determined amount, non-limiting examples of which include 1 yard, 2 yards, 3 yards, 4 yards, 5 yards, 10 yards, 15 yards, 20 yards, 25 yards, 30 yards, 35 yards, 40 yards, 50 yards, 60 yards, 70 yards, 75 yards, 80 yards, 85 yards, 90 yards, 95 yards, or 100 yards (i.e. y=−1, −2, . . . −100, respectively), or to a value equivalent with the difference in elevation between the golfer and the golf target.

Some golf ball launch tracking systems only provide the ball speed and launch angle. Consequently, for each club and in another embodiment, the initial backspin rate of the ball at impact can be determined by accessing a database of golf ball launch data accumulated for other golfers, and selecting an initial backspin rate associated with one or more golf shots having a similar ball speed and launch angle. In some embodiments, the initial backspin rate selected from the database can be determined from shots taken with a golf club either equivalent or similar to the club used by the golfer. As a non-limiting example, when trying to determine the backspin rate of a golfer's 7-iron, the backspin rate selection can be made from golf ball launch data collected for 7-iron shots.

In another embodiment, the initial backspin rate selected from the database can be determined based on the loft of the club. Generally, the lofts of golf clubs are not consistent from manufacturer to manufacturer, or even between different models of golf clubs from the same manufacturer. For example, the pitching wedge associated with one manufacturer's iron set can have a 41° loft angle, while the golf club of another manufacturer that has the same 41° loft angle is a 9-iron. Accordingly, in a non-limiting example, the backspin rate of a golfer's 41° pitching wedge can be determined from golf ball launch data from any club having the same loft angle, independently of the name of the club. In another embodiment, more golf ball launch data can be accumulated by expanding the search to lofts that are above or below the given loft, non-limiting examples of which can be +/−0.5°, 1°, 1.5°, or 2°. In another embodiment, loft angle and club identity (above) can both be utilized as search criteria for selecting an initial backspin.

In some embodiments, any of the golf ball launch data described above can be included in the mathematical approximation in addition to the launch angle, backspin, and ball speed. In one non-limiting example, the side spin of the ball, $F_{side\ spin}$ can be incorporated into the approximation to facilitate the modeling of the trajectory in three dimensions.

In combination with the backspin, the side spin defines a spin-tilt axis around which the golf ball rotates, which determines the direction and curvature of the golf ball's trajectory. As a result, at any point in time $t_n$ in the golf ball's trajectory, the golf ball can additionally have a z-coordinate position, in which the z-axis is defined by a horizontal line perpendicularly to the golf target and the y-axis; a velocity; and an angle $\psi$, in the x-z plane. At $t_0$, the $\psi$ angle can be determined using a launch monitor, based in part on the club's typical path, face angle, $F_{side\ spin}$ at impact. At time $t_{n+1}$, the $\psi$ angle can be calculated similarly to the $\varphi$ angle, except that the angular velocity component, $\omega$, of the $F_{side\ spin}$ is measured in either a clockwise or counterclockwise direction, while the z-coordinate position can be calculated using the following equation:

$$y_{n+1(Z)} = y_{n(Z)} + (\overline{V}_n * \sin \psi_n) \qquad (23)$$

Without being limited by a particular theory, it is believed that the curvature of the golf ball can have an effect on both the height of the golf shot as well as the distance. For example, hitting a draw shot, which curves to the left for a right-handed golfer and to the right for a left-handed golfer, often results in an increase in distance and a lower shot height relative to a straight shot. On the other hand, a fade shot, which curves to the left for a right-handed golfer and to the right for a left-handed golfer, often results in a decrease in distance and an elevated shot height relative to a straight shot.

Similarly, environmental data measured by one or more sensors associated with the rangefinder device or portable computing device, or retrieved from one or more data sources (e.g. the Internet), can be utilized in the modeling of a golf ball trajectory. The one or more sensors can be selected from the group comprising an inclinometer, a GPS receiver, a temperature sensor, a humidity sensor, an altimeter, an anemometer, a compass, and a barometer. Non-limiting examples of environmental data that can be measured by the one or more sensors or retrieved one or more data sources can include temperature, humidity, altitude, barometric pressure, and precipitation, each of which can be utilized directly or indirectly to determine the dynamic pressure, q, in equations (14) and (19) above.

In another non-limiting example, the wind speed and direction, collected by any of the sensors or data sources described above, can also be utilized to predict the golf ball's trajectory. Based on the wind speed and direction, the golf ball's trajectory can be affected both horizontally relative to the target line and vertically. Generally, deflection of the trajectory horizontally is caused by drag, which is applied across the ball in the same direction as the wind. Similarly, the wind can increase or decrease the $F_{lift}$, based on the direction and intensity of the wind. Without being limited by a particular theory, it is believed that when the ball is spinning in a clockwise rotation, such as in a fade or slice, the Magnus effect-induced pressure differences as a result of the wind can impart a force either a downward force (in a right-to-left wind) or an upward force (in a left-to-right wind) perpendicular to the sideways vector of the wind, and that the converse is true when the ball is spinning in a counter-clockwise rotation, such as in a draw or hook.

Without being limited by a particular theory it is also believed winds with a headwind component (i.e. winds blowing away from the target) or tailwind component (i.e. winds blowing toward the target) can cause an increase or decrease in the backspin of the golf ball, affecting the $F_{lift}$, the overall hangtime of the ball in the air, and the trajectory itself, particularly as the ball travels downward from its apex. With respect to a headwind, it is believed that a headwind can increase backspin, maintaining the flight of the ball in the air longer as a result of the increase in the $F_{lift}$, and steepening the downward trajectory of the ball from its apex. As a result of a longer hangtime, there is also more opportunity for the wind to impart a force against the ball and away from the target, reducing the distance of the shot. On the other hand, with respect to a tailwind, it is believed that a tailwind component can decrease backspin, causing a shorter hangtime and a flatter downward trajectory of the ball from its apex. However, the force of the wind in the same relative direction as the target can cause an increase in the shot distance.

The force of the wind, or $F_{wind}$, can be calculated from the wind speed according to the following equation:

$$F_{wind} = C_{d,wind} * v_{wind} \quad (24)$$

wherein $v_{wind}$ is the wind speed and $C_{d,wind}$ is the drag coefficient for the wind. In some embodiments, the wind direction can also be defined by an angle α in the x-z plane, such that the x-axis component and the z-axis component of the $F_{wind}$ on the ball can be defined by the following equations:

$$F_{wind(X)} = \sin \alpha * (C_{d,wind} * v_{wind}) \quad (25)$$

$$F_{wind(Z)} = \cos \alpha * (C_{d,wind} * v_{wind}) \quad (26)$$

In another embodiment, the golf ball's velocity and angle-of-flight p can be calculated upon taking into account the effect of the $F_{wind}$ on both $F_{drag}$ and $F_{lift}$, particularly as a result of change in the ball's spin rate, which is utilized to determine the ball's rotational speed ratio, $\omega_r$. Further, and in another embodiment, while the $y_{n+1(Y)}$ position can be calculated similarly to above, using the wind-affected golf ball velocity, the z- and z-axis positions of the golf ball can be calculated upon determining $F_{wind(X)}$ and $F_{wind(Z)}$, according to the following equations:

$$y_{n+1(X)} = y_{n(X)} + (\overline{V}_n * \cos \varphi_n) + F_{wind(X)} \quad (27)$$

$$y_{n+1(Z)} = y_{n(Z)} + (\overline{V}_n * \sin \varphi_n) + F_{wind(Z)} \quad (28)$$

Without being limited by a particular theory, it is believed that the trajectories predicted by any of the mathematical approximation methods described above and as illustrated in FIG. 8 and FIG. 9, better simulate the real-world trajectories of golf shots than the parabolic or polynomial trajectories illustrated in U.S. Pat. Nos. 7,239,377, 7,535,553, 7,859, 650, and 8,314,923, above. By accounting for the effect of the Magnus force, it is believed that trajectories modeled according to the methods and systems of the present invention generally exhibit an increase in the φ angle after an initial launch phase, as well as a steep downward trajectory (i.e. a −φ angle) after reaching the apex, as a result of solving for $F_{lift}$. In contrast, it is believed both the upward and downward trajectories of golf shots predicted by classical polynomial modeling, which do not account for $F_{lift}$, are generally less steep.

In some embodiments, the one or more modeled trajectories can be retrieved from a memory housed within either the rangefinder device or the portable computing device. In a non-limiting example, trajectories can be retrieved from a memory when the trajectories are modeled in two dimensions and/or environmental data is not utilized. In some embodiments, each trajectory can be modeled ad hoc, prior to each shot. In some embodiments, environmental data can be utilized in the modeling of each trajectory, upon retrieving the environmental data from the one or more sensors or one or more data sources. In further embodiments, wind data is used to determine the trajectory for particular golf shot. In some embodiments, course data, such as the GPS location of either or both of the golfer or the target, as well as the terrain in either location, can be utilized in the modeling of each trajectory. Such course data can be obtained from a memory or data source, or by user input. In a non-limiting example, a golfer can indicate the type of lie (e.g. fairway, rough, sand, etc.) or the slope of the lie (uphill, downhill, and/or sidehill).

In another embodiment, the golfer can input a desired shot height relative to their typical shot height, such as to avoid obstacles or to take advantage of a particular course terrain feature or environmental conditions, such as a downslope, tailwind, etc. Non-limiting examples of such selections for shot height are "normal," "high," "low," and the like. In another embodiment, upon selecting a "higher" or "lower" desired shot height, a golf ball trajectory can be modeled based on an increase or decrease in the launch angle relative to a golfer's normal trajectory. For example, and in another embodiment, if a golfer desires a higher trajectory, the initial launch angle for a golf shot with a particular golf club can be increased by an amount selected from the group consisting of at least 0.5°, at least 1°, at least 1.5°, at least 2°, at least 2.5°, at least 3°, at least 3.5°, at least 4°, at least 4.5°, at least 5°, or at least 10°, when calculating the adjusted trajectory. For example, and in another embodiment, if a golfer desires a lower trajectory, the initial launch angle for a golf shot with a particular golf club can be decreased by an amount selected from the group consisting of at least 0.5°, at least 1°, at least 1.5°, at least 2°, at least 2.5°, at least 3°, at least 3.5°, at least 4°, at least 4.5°, at least 5°, or at least 10°, when calculating the adjusted trajectory.

In another embodiment, the initial backspin can also be increased or decreased as a result of selecting a higher- or lower-trajectory golf shot. Without being limited by a particular theory, it is believed that increasing the backspin can result in a higher trajectory than a normal golf shot, whereas decreasing the backspin can result in a lower trajectory than a normal golf shot. In some embodiments, if a golfer desires a higher trajectory, the initial backspin for a golf shot with a particular golf club can be increased by an amount selected from the group consisting of at least 100 rpm, at least 200 rpm, at least 300 rpm, at least 400 rpm, at least 500 rpm, at least 600 rpm, at least 700 rpm, at least 800 rpm, at least 900 rpm, at least 1000 rpm, or at least 2000 rpm, when calculating the adjusted trajectory. In some embodiments, if a golfer desires a lower trajectory, the initial backspin for a golf shot with a particular golf club can be decreased by an amount selected from the group consisting of at least 100 rpm, at least 200 rpm, at least 300 rpm, at least 400 rpm, at least 500 rpm, at least 600 rpm, at least 700 rpm, at least 800 rpm, at least 900 rpm, at least 1000 rpm, or at least 2000 rpm, when calculating the adjusted trajectory. In some embodiments, when adjusting the trajectory higher or lower relative to normal, the launch angle, the initial spin, or both, can be adjusted as needed.

Once the mathematical approximation is performed to model each personalized trajectory for one or more golf clubs, each of the trajectories can be inserted into an x,y-coordinate system along with a golf target to begin determining the AYR. In some embodiments, trajectories that are modeled in three dimensions can be projected into the x,y plane prior to determining the AYR. In one non-limiting example, the processor selects a club that has an average distance, $\overline{x}$, that is greater than the horizontal distance to the target, x. In some embodiments, the average distance, $\overline{x}$, is the golfer's average carry distance with a particular club. In some embodiments, the the average distance, $\bar{x}$, is the golfer's average total distance with a particular club. The modeled trajectory of a golf shot taken with that club is then compared with the target's x,y-coordinate position, to determine if there is a point (x',y') along the trajectory such that when y' is equal to y (the elevation of the target), the trajectory either passes through the target point (x'=x), or extends past the target point (x'>x). In some embodiments, the processor can select one or more clubs with a longer average distance, $\bar{x}$, and compare that trajectory with the target to determine whether there is a point a point (x',y') such that when y' is equal to y, x' is greater or equal to x. In some embodiments, the next furthest club (e.g. a 7-iron relative to an 8-iron) is selected, and if x' is still less than x, then the next club (e.g. a 6-iron) and/or successive clubs can be selected until a trajectory is found such that when y' is equal to y, x' is greater or equal to x.

In some embodiments, the effect of the wind on the AYR can be approximated by adding or subtracting the magnitude of the wind along the path of the intended shot, $F_{wind(X)}$. In one non-limiting example, if the wind has a tailwind component, the adjusted AYR can be expressed by the following equation:

$$AYR_{wind} = AYR - F_{wind(X)} \quad (29)$$

In another non-limiting example, if the wind has a headwind component, the adjusted AYR can be expressed by the following equation:

$$AYR_{wind} = AYR + 2 \times F_{wind(X)} \quad (30)$$

Figure 10:
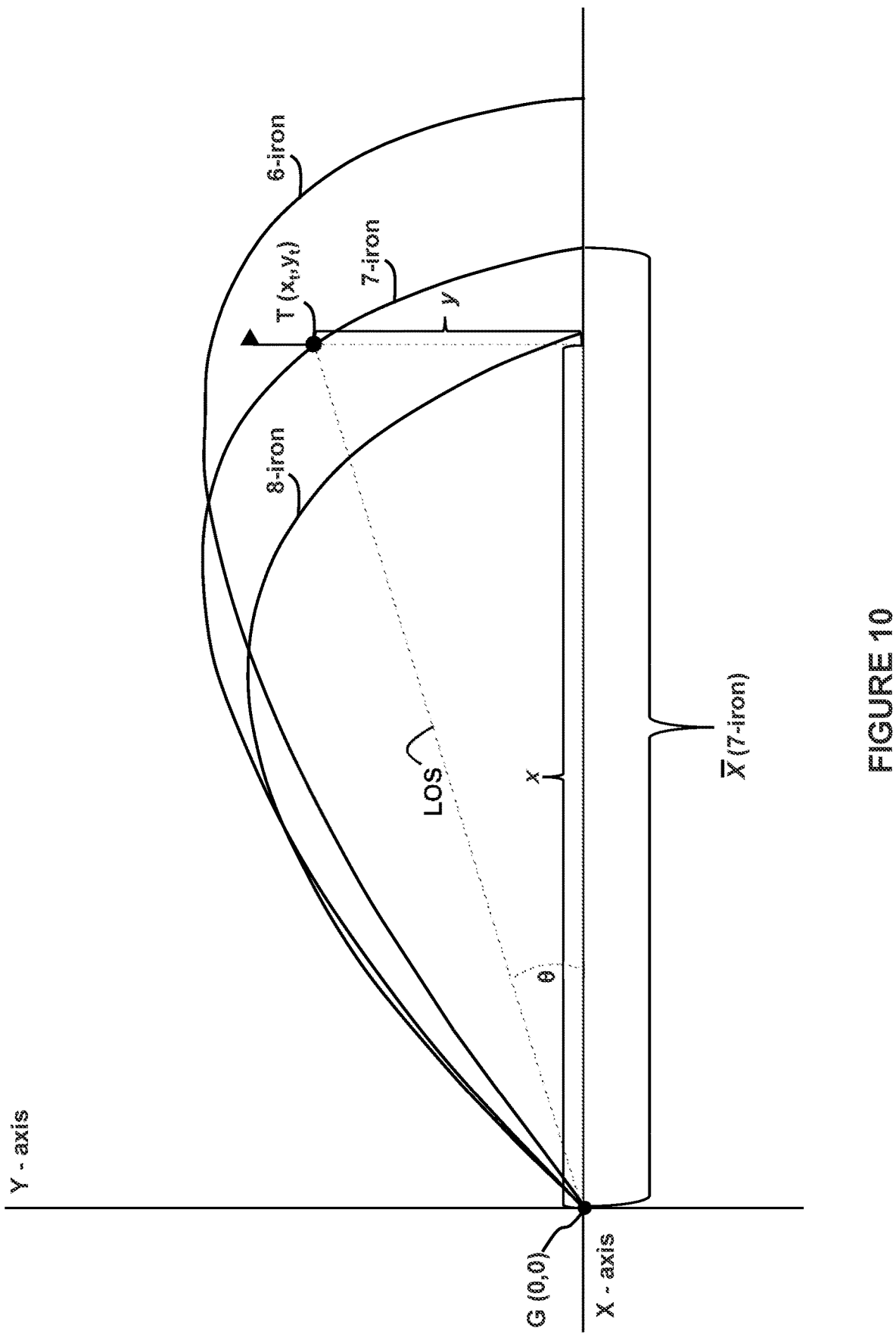
FIG. 10 illustrates the use of a golfer's discretized trajectories to provide an AYR to an uphill golf target, in which one of the trajectories pass directly through a target.

A non-limiting example of an AYR determination for a golf shot to a pin, T, at position $(x_t, y_t)$, located on an elevated green, without wind, is shown in FIG. 10. The first club with an average carry distance, $\bar{x}$, further than the horizontal distance, x, to the target is an 8-iron. However, because the flag is elevated relative to the golfer, the golfer's modeled 8-iron trajectory does not reach the flag. As a result, the trajectory for the 7-iron is selected and compared with the flag. As illustrated in FIG. 10, the 7-iron trajectory is modeled to land at the same location as the flag (i.e. x'=x; y'=y). Consequently, the AYR is identical to the golfer's average carry distance, $\bar{x}$, of their 7-iron.

Figure 11:
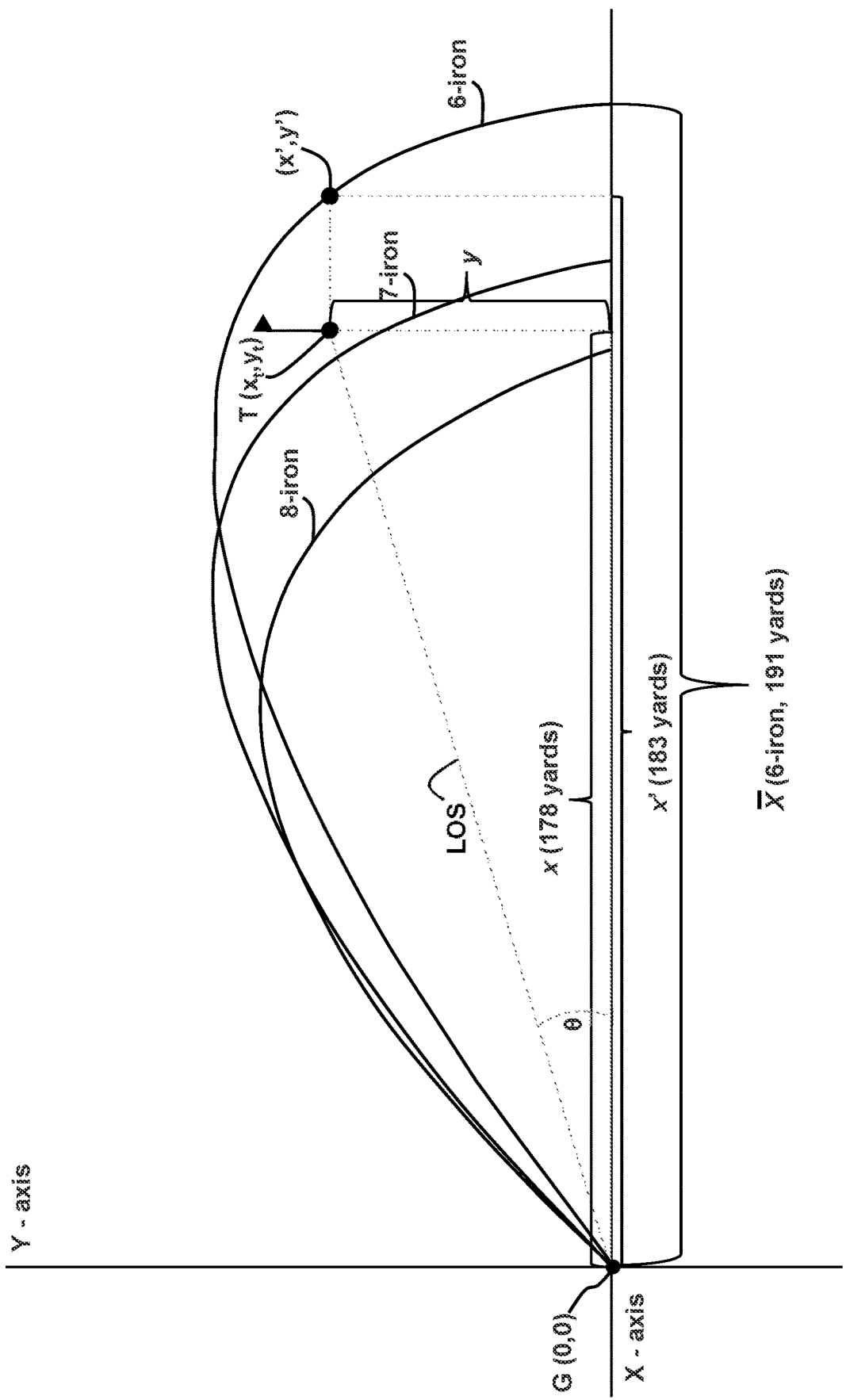
FIG. 11 illustrates the use of a golfer's discretized trajectories to provide an AYR to an uphill golf target, in which one of the trajectories extends past the target.

Another non-limiting example of an AYR determination for a golf shot to a flag on an elevated green is shown in FIG. 11. As illustrated, both the 8-iron and the 7-iron have an average carry distance, $\bar{x}$, that is further than the horizontal distance, x, to the flag, but fail to reach the flag as a result of the flag's elevation. The 6-iron trajectory extends past the flag, such that when y' is equal to y, x' is greater than x. As a result, the 6-iron is selected for determining the AYR. In some embodiments, when x' is greater than x, the AYR can be determined using the following equation:

$$AYR = \bar{x} \cdot \left(\frac{x}{x'}\right) \quad (31)$$

For example, in FIG. 11, if the horizontal distance to the pin, T, is 178 yards, the distance that the trajectory has the same y value as the flag (x') is 183 yards, and the golfer's average shot distance with a 6-iron is 191 yards, then the AYR is $$191 \cdot \left(\frac{178}{183}\right),$$

or 185.8 yards. Accordingly, the AYR number is equivalent to the distance that a golfer would have to hit the ball to a target that is at the same elevation as the golfer (i.e. y=0).

In another embodiment, even if the initial club selection does result in a trajectory having a point (x',y') such that when y' is equal to y, x' is greater or equal to x, the processor can also select one or more clubs with a shorter average distance (e.g. an 7-iron relative to a 6-iron), to determine if that club's shot trajectory is also predicted to reach the target. If the trajectory of one or more of the shorter clubs does reach the target, then any of those clubs can be selected. In some embodiments, the shortest club that reaches the target is selected. Referring back to FIG. 10, if a 6-iron is selected in an initial step, the modeled trajectory for the 6-iron extends past the x,y-position of the flag. In a succeeding step, the modeled trajectory for a 7-iron is then compared with the position of the flag. Because the 7-iron trajectory passes directly through the target, the AYR is identical to the golfer's average carry distance, $\bar{x}$, of their 7-iron, as described above. Conversely, and referring back to FIG. 11, once the 6-iron trajectory is determined to extend past the flag, the 7-iron trajectory can be compared to the flag's x,y-position. Because the modeled trajectory for the 7-iron did not reach the target (x'<x), the 6-iron is selected for calculating the AYR, as described above.

Figure 12:
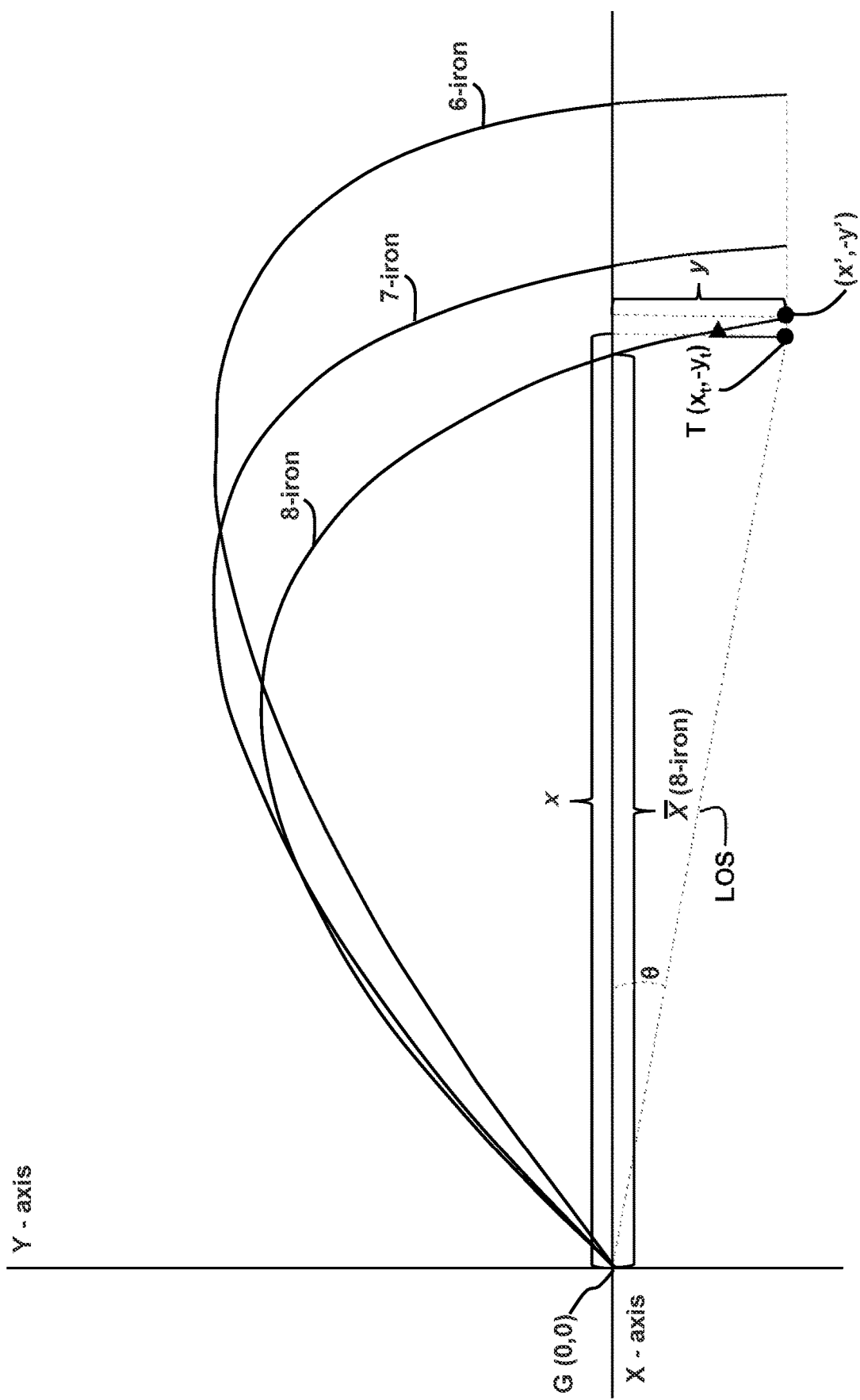
FIG. 12 illustrates the use of a golfer's discretized trajectories to provide an AYR to a downhill golf target, in which all of the trajectories extend past the target.

In another non-limiting example, an AYR for a golf shot from an elevated position to a flag or target below can also be determined. As illustrated in FIG. 12, the target is pin, T, at position $(x_t, -y_t)$. Upon determining the elevation of the golfer relative to the target based on the LOS distance and the downward angle, the golf ball trajectory is modeled as described above, except that the trajectory is extended past the x-axis until reaching or extending past the same elevation as the target. Even though the target is at the point (x,-y), the AYR is still determined based on determining whether the trajectory has a point (x',y') such that when y' is equal to y (i.e. -y), x' is greater or equal to x. In FIG. 12, the 8-iron's trajectory is the shortest club that extends past the target, and is accordingly used to calculate the AYR according to Equation 31, above.

Figure 13:
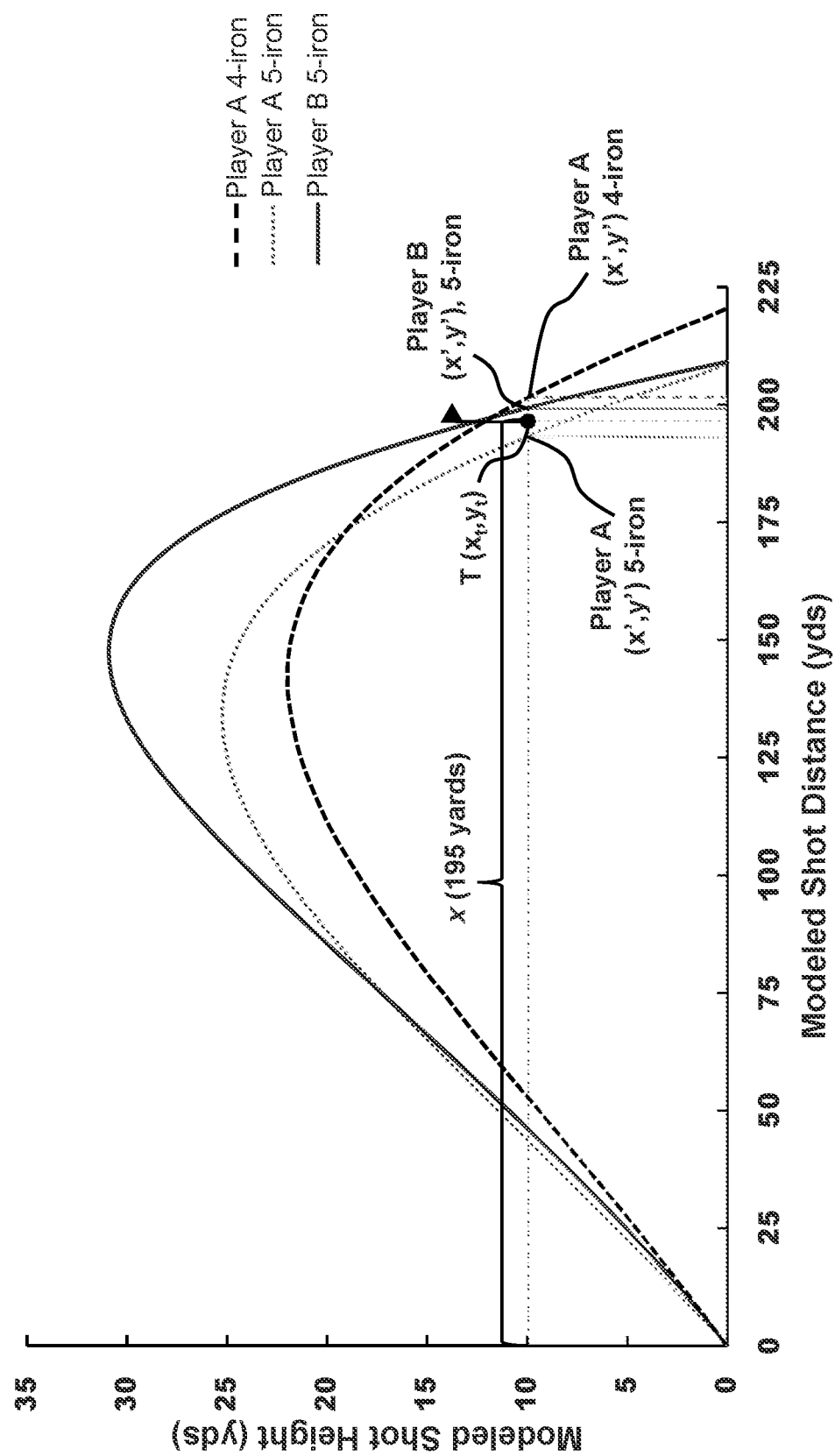
FIG. 13 illustrates the effect of trajectory shape on providing an AYR to two golfers who hit the same golf club an identical distance.

Without being limited by a particular theory, it is believed that a golfer's modeled or simulated trajectories for each golf club, particularly when calculated based on golf ball launch data that has been collected by a launch monitor or similar system, is unique relative to other golfers. As a result, a golfer's unique trajectory can result in a different AYR relative to a second golfer, even if the second golfer hits the same club (e.g. a 5-iron) the same average distance. In a non-limiting example and as illustrated in FIG. 13, player A and player B both have an average carry distance for a 5-iron of 210 yards, and the modeled trajectories for each player's 5-iron indicate that Player B hits the ball much higher than Player A. The target, T $(x_t, y_t)$, is approximately 195 yards away at an elevation of 10 yards, relative to the golfer. Player B's 5-iron trajectory extends past the target such that the ball is at the same elevation as the target at an x' of 199 yards. As a result, the AYR for Player B is $$210 \cdot \left(\frac{195}{199}\right),$$

or 205.7 yards. On the other hand, Player A's shot with a 5-iron is modeled to come short of the target, as a result of the flatter ball flight relative to Player B. The trajectory for Player A's 4-iron ($\bar{x}$=220 yards) is then compared against the position of the target, and can be used to calculate the AYR, since the trajectory has an x' of 203 yards. As a result, the AYR for Player A is $$220 \cdot \left(\frac{195}{203}\right),$$

or 211.3 yards.

It is also believed that the AYR's for Player A and Player B described above and illustrated in FIG. 13 are more accurate and tailored to each individual golfer, relative to adjusted distances calculated using classical methods based on the angle to the target and LOS distance, as described above. In the above example, since the target is 195 yards away at an elevation of 10 yards, the θ angle is 9 degrees and the LOS distance is 195.3 yards. As a result, the adjusted distance to the target calculated by classical methods for both Player A and Player B is (195.3×cos(9))+(195.3×sin (9)), or 223.4 yards. Both Player A and Player B would think that they have to use an identical club, when in fact they need different clubs. None of the devices or methods described in U.S. Pat. Nos. 7,239,377, 7,535,553, 7,859,650, or 8,314,923, incorporated by reference above, account for the differences in each golfer's trajectory shape. Consequently, these devices and others known in the art are often providing impersonal, inaccurate, and/or misleading adjusted yardages, particularly for targets that are significantly above or below the target.

Furthermore, it is believed that upon a golfer exchanging a first golf club for a second golf club of the same type, the golfer's predicted trajectory with the second golf club may change relative to the first club. As a non-limiting example, if a golfer replaces his or her driver with a newly-purchased driver, the modeled trajectory with the new driver can be different than the trajectory modeled for the previous driver. In some embodiments, a new trajectory can be modeled each time a golfer provides golf ball launch data for a new club. In some embodiments, golf ball launch data and/or predicted trajectories for previous clubs can be stored in the memory of the rangefinder device or the portable computing device. In some embodiments, previous golf ball launch data and/or predicted trajectories can be stored in the memory of the rangefinder device or the portable computing device after the golfer's golf ball launch data is updated for the same golf club or set of clubs.

In another embodiment, all of the method steps for determining and providing an AYR are performed by a processor contained within the rangefinder device itself, without the need for a portable computing device. In another embodiment, a golfer may use a laser rangefinder device to determine the LOS distance and angle of elevation to the target, and communicate the same to the portable computing device. Upon determining the AYR, the portable computing device can communicate the AYR back to the rangefinder device and indicated on the rangefinder display and/or display the AYR on the display of the portable computing device. In another embodiment, a portable computing device can be utilized to retrieve the angle of elevation and LOS distance to the target, perform the one or more mathematical approximations to model golf ball trajectories, and calculate the AYR, with the need for a rangefinder.

While particular embodiments of the invention have been described, the invention can be further modified within the spirit and scope of this disclosure. Those skilled in the art will recognize, or be able to ascertain using no more than routine experimentation, numerous equivalents to the specific procedures, embodiments, claims, and examples described herein. As such, such equivalents are considered to be within the scope of the invention, and this application is therefore intended to cover any variations, uses or adaptations of the invention using its general principles. Further, the invention is intended to cover such departures from the present disclosure as come within known or customary practice in the art to which this invention pertains and which fall within the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The contents of all references, patents, and patent applications mentioned in this specification are hereby incorporated by reference, and shall not be construed as an admission that such reference is available as prior art to the present invention. All of the incorporated publications and patent applications in this specification are indicative of the level of ordinary skill in the art to which this invention pertains, and are incorporated to the same extent as if each individual publication or patent application was specifically indicated and individually indicated by reference.

We claim:

1. A system for providing a golfer with an adjusted distance for a golf shot to a target on a golf course, the system comprising:
   a. a laser rangefinder comprising:
      i. a sensor comprising a range sensor for determining a line-of-sight (LOS) distance and an inclinometer for determining an angle of elevation from the laser rangefinder to a golf target on a golf course, prior to a golfer taking a golf shot;
      ii. a first wireless external device interface;
      iii. a rangefinder display;
      iv. a first processor in electronic communication with each of the sensor, the display, and the wireless external device interface;
   b. a launch monitor that directly measures a golf ball launch data during a golf shot by a golfer, the golf ball launch data comprising at least one of an initial ball speed, an initial backspin rate, and a launch angle; and
   c. a mobile phone comprising:
      A. a memory for storing the golf ball launch data and computer-readable instructions for determining the adjusted distance from the laser rangefinder to the golf target;
      B. a phone display;
      C. a second wireless external device interface in electronic communication with the first wireless external device interface; and
      D. a second processor in electronic communication with each of the memory, the phone display, and the second wireless external device interface, for retrieving the golf ball launch data and the computer-readable instructions from the memory, and a LOS distance and the angle of elevation to the golf target from the laser rangefinder, automatically executing the computer-readable instructions retrieved from the memory to generate an adjusted distance from the laser rangefinder to the golf target using the golf ball launch data of the golfer, the LOS distance, and the angle of elevation, wherein the adjusted distance from the laser rangefinder to the golf target is unique to the golfer, wirelessly transmitting the adjusted distance from the second processor to the first processor, wherein the first processor electronically communicates the adjusted distance to the rangefinder display.

2. The system according to claim 1, wherein the first wireless external device interface and the second wireless external device interface electronically communicate with each other using a BlueTooth® communication protocol.

3. The system according to claim 1, wherein the second processor additionally retrieves environmental data for the golf course and utilizes the environmental data to automatically generate the adjusted distance, wherein the adjusted distance is unique to the golfer and the environmental data, and the environmental data is selected from the group consisting of the temperature, humidity, altitude, wind speed, wind direction, compass direction, and barometric pressure, and a combination thereof.

4. The system according to claim 1, wherein the launch monitor further measures the golfer's side spin rate, and the golf ball launch data further comprises the spin rate.

5. A method for providing a golfer with an adjusted distance for a golf shot to a target on a golf course, the method comprising the steps of:
   a. providing a launch monitor that directly measures golf ball launch data of a golfer during a golf shot, the golf ball launch data comprising at least one of an initial ball speed, an initial backspin rate, and a launch angle;
   b. hitting, by the golfer, one or more golf shots in the presence of the launch monitor to collect the golf ball launch data of the golfer;
   c. prior to a golf shot by the golfer on a golf course, determining a line-of-sight (LOS) distance and angle of elevation from a laser rangefinder used by the golfer to a golf target, the laser rangefinder comprising a sensor comprising a range sensor and an inclinometer, a display, a first wireless external device interface, and a first processor in electronic communication with each of the sensor, the display, and the first wireless external device interface;
   d. wirelessly transmitting, using the first wireless external device interface, the LOS distance and angle of elevation from the laser rangefinder to a portable computing device, the portable computing device comprising:
   a second wireless external device interface in electronic communication with the first wireless external device interface;
   a memory, wherein the memory stores the golf ball launch data of the golfer and computer-readable instructions for determining an adjusted distance from the laser rangefinder to the golf target, and
   a second processor in electronic communication with each of the second wireless external device interface and the memory, wherein the second processor retrieves from the memory the golf ball launch data of the golfer and computer-readable instructions for determining an adjusted distance from the memory, and automatically executes the computer-readable instructions retrieved from the memory to generate an adjusted distance from the laser rangefinder to the golf target using the golf ball launch data of the golfer, the LOS distance, and the angle of elevation;
   e. wirelessly transmitting, from the second wireless external device interface to the first wireless external device interface, the adjusted distance from the laser rangefinder to the golf target; and
   f. indicating on the display the adjusted distance from the laser rangefinder to the golf target;
   wherein the adjusted distance from the laser rangefinder to the golf target is unique to the golfer.

6. The method according to claim 5, wherein the second processor additionally retrieves environmental data for the golf course and utilizes at least a portion of the environmental data to generate the adjusted distance from the golfer to the golf target,
   wherein the adjusted distance is unique to the golfer and the environmental data, and
   wherein the environmental data is selected from the group consisting of the temperature, humidity, altitude, wind speed, wind direction, compass direction, and barometric pressure, including combinations thereof.

7. The method according to claim 6, wherein at least a portion of the environmental data is wirelessly transmitted from the second wireless external device interface to the first wireless external device interface and is indicated on the display.

8. The method according to claim 6, wherein the environmental data comprises wind speed and wind direction.

9. The method according to claim 8, wherein the wind speed and wind direction are wirelessly transmitted from the second wireless external device interface to the first wireless external device interface and is indicated on the display.

10. The method according to claim 5, wherein the first wireless external device interface and the second wireless external device interface electronically communicate with each other using a BlueTooth® communication protocol.

11. The method according to claim 5, wherein the portable computing device is a mobile phone.

12. The method according to claim 5, wherein the golf ball launch data measured by the launch monitor further comprises a side spin rate.

13. The method according to claim 5, wherein the golf target is a pin positioned on a golf green.

14. A laser rangefinder for providing a golfer with an adjusted distance for a golf shot to a target on a golf course in real-time, wherein the adjusted distance is personalized to the golfer and the laser rangefinder comprises:
   a sensor, the sensor comprising a range sensor for determining a line-of-sight (LOS) distance from the laser rangefinder to the target and an inclinometer for determining an angle of elevation from the laser rangefinder to the target;
   a display;
   a first external device interface;
   a first processor; and
   a first non-transitory computer-readable storage medium to direct the first processor to:
     actuate the range sensor to obtain the LOS distance to the target;
     actuate the angle sensor to obtain the angle of inclination to the target;
     output the LOS distance and angle of elevation to a portable computing device, the portable computing device comprising;

a second external device interface;

a second processor; and a second non-transitory computer-readable storage medium, the second storage medium comprising the golfer's golf ball launch data, the golf ball launch data previously collected by a launch monitor and comprising at least one of an initial ball speed, an initial backspin rate, and a launch angle, wherein the second storage medium directs the second processor to:

obtain the golfer's golf ball launch data from the second storage medium;

generate the golfer's adjusted distance using the golfer's golf ball launch data, the LOS distance, and the angle of elevation; and output the golfer's adjusted distance to the laser rangefinder; and indicate the golfer's adjusted distance on the display.

15. The laser rangefinder of claim 14, wherein the second storage medium comprises instructions to direct the second processor to further obtain real-time environmental data for the golf course and utilize the environmental data when generating the golfer's adjusted distance, wherein the environmental data is selected from the group consisting of the temperature, humidity, altitude, wind speed, wind direction, compass direction, and barometric pressure, including combinations thereof.

16. The laser rangefinder of claim 15, wherein:

the second storage medium comprises instructions to direct the second processor to output the environmental data to the laser rangefinder, and the first storage medium comprises instructions to direct the first processor to indicate the environmental data on the display.

17. The laser rangefinder of claim 14, wherein the first wireless external device interface and the second wireless external device interface electronically communicate with each other using a BlueTooth® communication protocol.

18. The laser rangefinder of claim 14, wherein the portable computing device is a mobile phone.

19. The laser rangefinder of claim 14, wherein the golf ball launch data comprises the golfer's side spin rate.

20. The laser rangefinder of claim 14, wherein the second storage medium comprises instructions to:

direct the second processor to perform either a non-polynomial temporal discretization or a finite differences method to generate a personalized trajectory for a golf shot taken by the golfer, and generate the golfer's adjusted distance using the golfer's personalized trajectory.

* * * * *